(12) United States Patent
Rao et al.

(10) Patent No.: US 12,419,627 B2
(45) Date of Patent: Sep. 23, 2025

(54) FORESKIN MANIPULATOR

(71) Applicants: Rahul R. Rao, Phoenix, AZ (US); John Le, Phoenix, AZ (US); Keenan Woodburn, Phoenix, AZ (US)

(72) Inventors: Rahul R. Rao, Phoenix, AZ (US); John Le, Phoenix, AZ (US); Keenan Woodburn, Phoenix, AZ (US)

( * ) Notice: Subject to any disclaimer, the term of this patent is extended or adjusted under 35 U.S.C. 154(b) by 556 days.

(21) Appl. No.: 17/479,328

(22) Filed: Sep. 20, 2021

(65) Prior Publication Data

US 2022/0175365 A1 Jun. 9, 2022

Related U.S. Application Data

(63) Continuation-in-part of application No. 17/122,766, filed on Dec. 15, 2020, now Pat. No. 11,123,057.

(60) Provisional application No. 62/948,656, filed on Dec. 16, 2019.

(51) Int. Cl.
*A41B 9/12* (2006.01)
*A41B 9/02* (2006.01)
*A61B 17/02* (2006.01)
*A61F 5/451* (2006.01)
*A61B 17/00* (2006.01)

(52) U.S. Cl.
CPC .......... *A61B 17/0293* (2013.01); *A41B 9/023* (2013.01); *A61B 2017/00982* (2013.01)

(58) Field of Classification Search
CPC .. A41B 9/023; A41B 9/14; A41B 9/02; A41B 9/00; A41B 9/004; A41B 9/007; A41B 9/12; A41B 9/026; A41B 9/008; A61H 19/40; A61H 19/34; A61H 19/50; A61H 19/32; A61H 19/30; A61H 19/00; A61B 2017/00982
USPC .......... 600/39–41, 208; 2/403, 466; D2/711–713, 731
See application file for complete search history.

(56) References Cited

U.S. PATENT DOCUMENTS

| | | | | |
|---|---|---|---|---|
| 2,705,951 A | * | 4/1955 | Crowner | A61F 6/04 128/844 |
| 3,131,691 A | * | 5/1964 | Scott | A61F 5/41 600/39 |
| 3,893,455 A | * | 7/1975 | McNally | A61B 17/326 600/41 |

(Continued)

FOREIGN PATENT DOCUMENTS

| | | | |
|---|---|---|---|
| CN | 204635152 U | * | 9/2015 |
| CN | 205358243 U | * | 7/2016 |

(Continued)

*Primary Examiner* — Jessica Weiss
(74) *Attorney, Agent, or Firm* — Quarles & Brady LLP; Yakov S. Sidorin

(57) ABSTRACT

A device dimensioned to temporarily retract the foreskin of an uncircumcised penis to allow for the healing of an infection or disease affecting the skin of the glans of the penis, external urethral orifice and foreskin; and/or to treat at least one of phimosis and paraphimosis. The device may be configured to stretch and constrict as needed without creating too much pressure as to cut off circulation, and/or include non-elastic and/or elastic synthetic material. Device may be available at different sizes to the patient to ensure the best fit. Device may perform other foreskin manipulation procedures, such as pulling it forward as opposed to retracting the foreskin. The use of such device.

7 Claims, 17 Drawing Sheets

(56) References Cited

U.S. PATENT DOCUMENTS

| | | | | | |
|---|---|---|---|---|---|
| 3,920,007 | A | * | 11/1975 | Line | A61F 5/41 52/717.03 |
| 4,262,662 | A | * | 4/1981 | Allinson | A61F 5/41 600/39 |
| 4,615,337 | A | * | 10/1986 | Allinson | A61F 5/41 600/39 |
| 5,360,390 | A | * | 11/1994 | Maanum | A61F 5/41 600/39 |
| 5,819,323 | A | * | 10/1998 | Edenfield | A41B 9/02 2/403 |
| 6,308,342 | B1 | * | 10/2001 | Qi | A41B 9/02 2/403 |
| 7,802,577 | B2 | * | 9/2010 | Cvetanovic | A61F 5/41 600/38 |
| 2009/0318754 | A1 | * | 12/2009 | Ettmer | A61F 5/41 2/403 |
| 2011/0146695 | A1 | * | 6/2011 | Taouil | A61F 5/41 128/869 |
| 2019/0175383 | A1 | * | 6/2019 | Williams | A61F 5/37 |
| 2021/0100681 | A1 | * | 4/2021 | Miles | A41B 9/14 |

FOREIGN PATENT DOCUMENTS

| | | | | |
|---|---|---|---|---|
| CN | 205597133 | U | * | 9/2016 |
| CN | 206547885 | U | * | 10/2017 |
| CN | 209107698 | U | * | 7/2019 |
| CN | 110559131 | A | * | 12/2019 |
| CN | 214283319 | U | * | 9/2021 |

\* cited by examiner

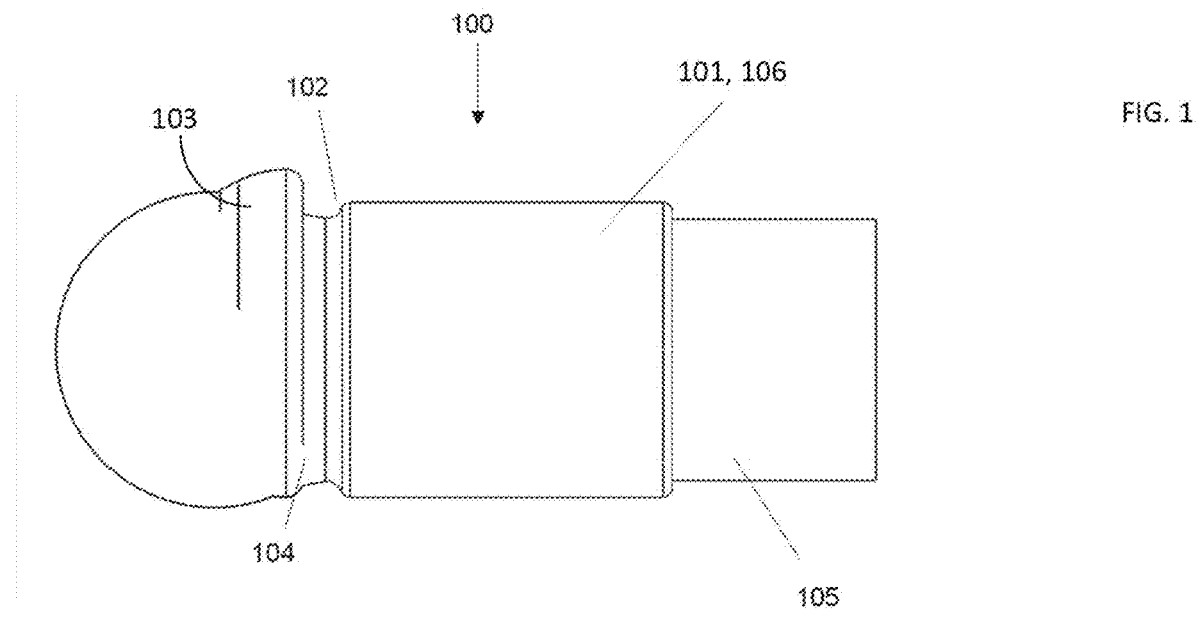
FIG. 1
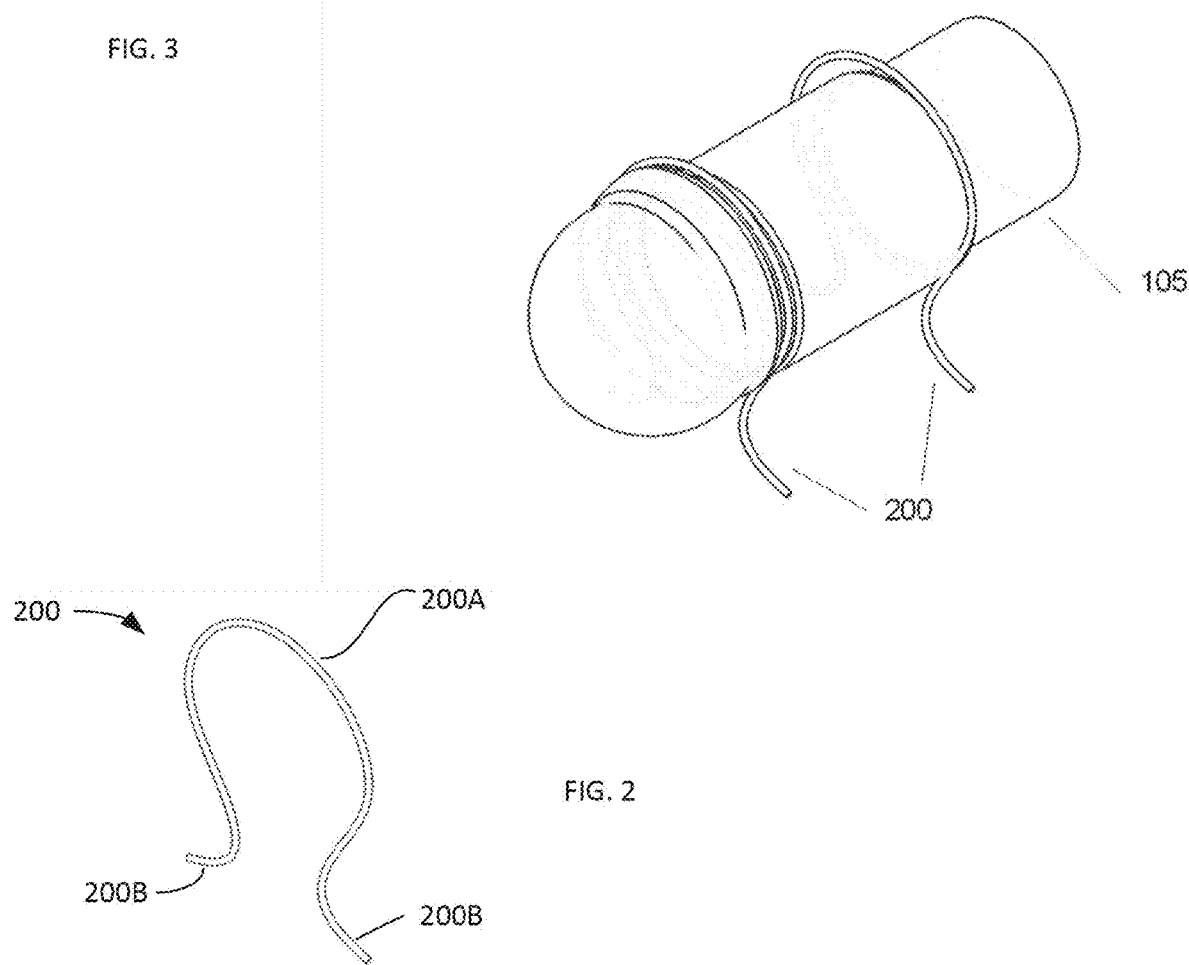
FIG. 3
FIG. 2

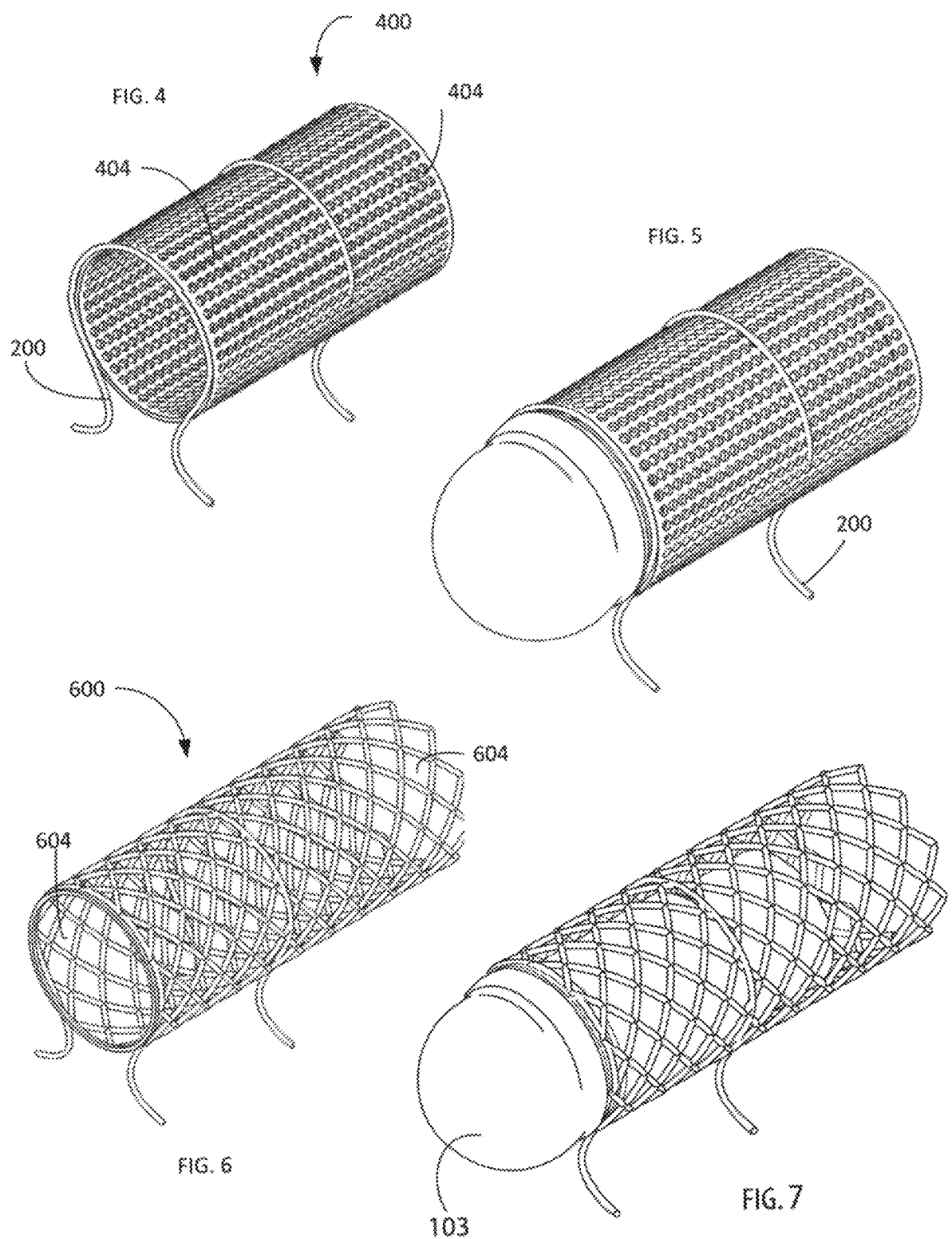

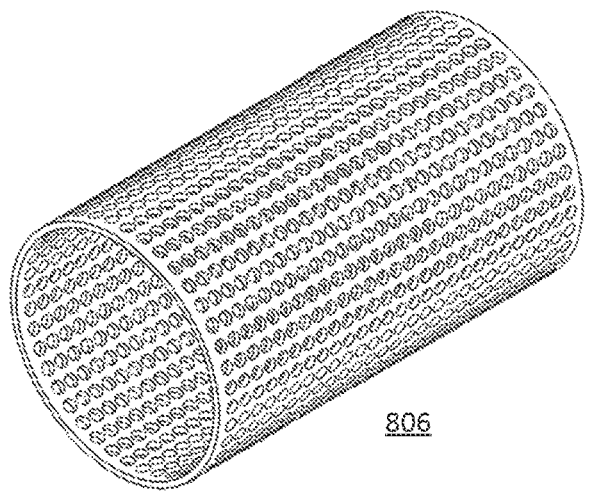
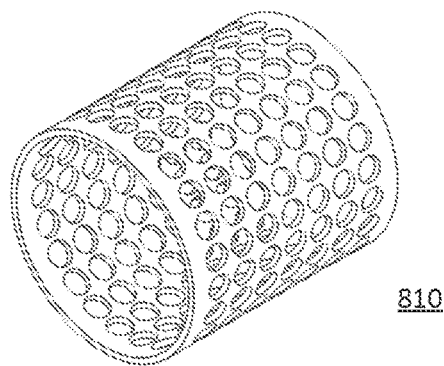
FIG. 8A    FIG. 8B
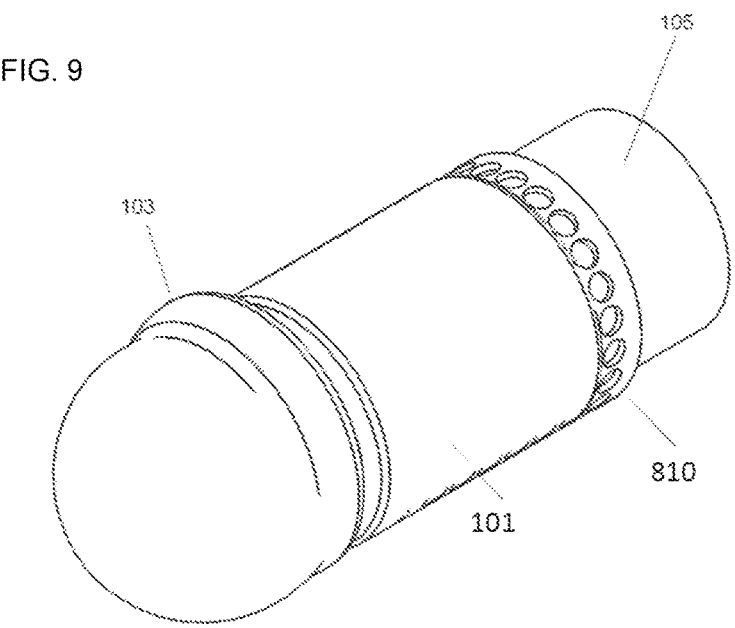
FIG. 9

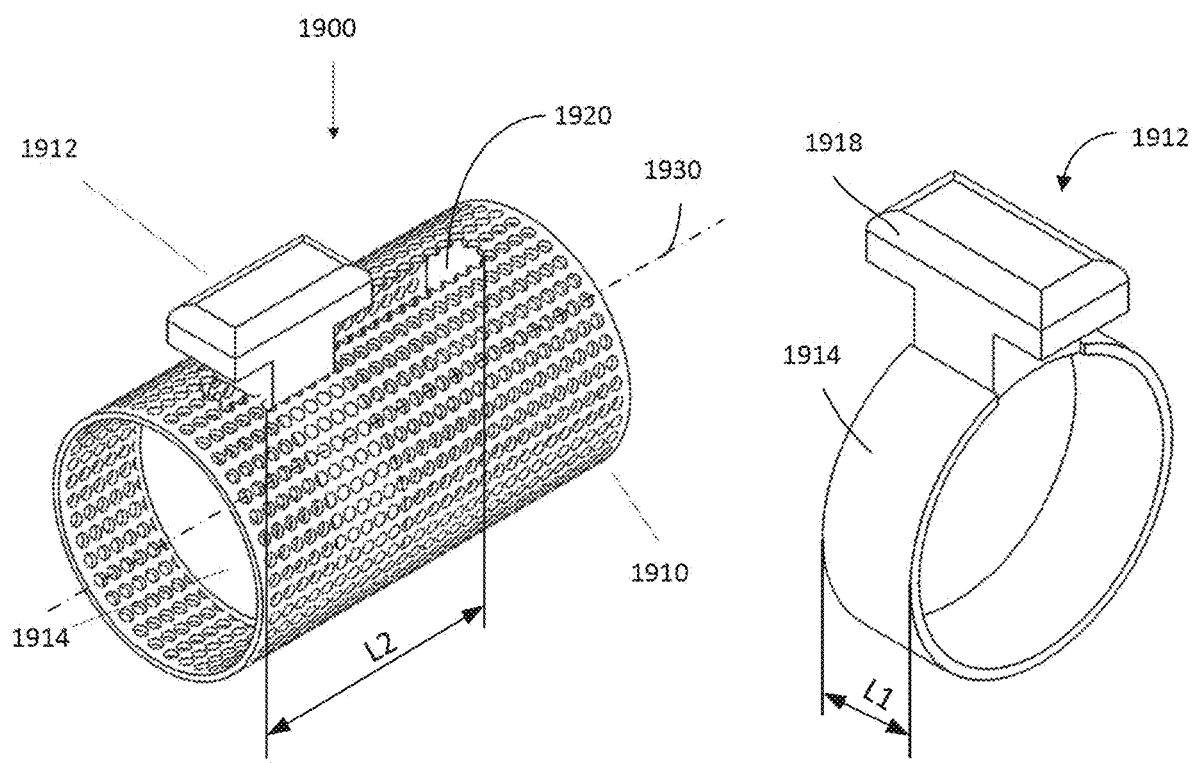

FORESKIN MANIPULATOR

CROSS-REFERENCE TO RELATED APPLICATIONS

This application is a continuation-in-part from the U.S. patent application Ser. No. 17/122,766 filed on Dec. 15, 2020 and now published as US 2021/0177392, which claims priority from the U.S. Provisional Patent Application No. 62/948,656 filed on Dec. 16, 2019. The disclosure of each of the above-identified patent documents is incorporated herein by reference.

TECHNICAL FIELD

The present invention relates to a nonsurgical medical treatment to achieve reversible retraction and inversion of penile foreskin to expose mucosal membranes of the penis in an uncircumcised male human and devices structured to achieve this goal. More particularly, the present invention is directed to correction of phimosis and/or paraphimosis and/or healing an infection or disease localized at/to the skin of the penis and foreskin of the penis.

RELATED ART

Among various infections that may affect the foreskin and the glans of the penis of an uncircumcised male there are Balanitis, Posthitis, Balanoposthitis, Lichen Sclerosis, Lichen Planus, Chancroids, Candida, Yeast Infection, Thrush, and Bacterial Infection. The most common recommended treatment for these diseases is the application of topical cream or ointment to the affected tissues including the mucosal membrane tissue of the foreskin when inverted. However, in an uncircumcised male these creams or ointments may be pushed off of the penis and foreskin by the foreskin itself in such a manner as to exit the body or by contact to surrounding clothing—this, understandably, limits the efficiency of the medical treatment. A sustained retraction of the foreskin could aid application of this topical cream and may speed up the healing process by promoting appropriate contact of the medication with the affected areas. While in severe cases circumcision may be recommended to limit the source of infection, it may not be the preferred solution for some patients who favor a nonsurgical approach. In these cases, the ability to temporarily retract the foreskin and sustain such retraction could be practically useful and equally curative.

SUMMARY OF THE INVENTION

Embodiments of the present invention provide is a penile foreskin retractor device configured to temporarily and reversibly retract and inverts the foreskin of an uncircumcised penis to expose the mucosal membranes and to allow for the healing of an infection or disease affecting anatomies of the penis such as the skin of the glans of the penis, external urethral orifice, and foreskin. Such diseases could include but are not limited to Balanitis, Posthitis, Balanoposthitis, Lichen Sclerosis, Lichen Planus, Chancroids, Candida, Yeast Infection, Thrush, and Bacterial Infection. The device is also configured to alleviate and/or correct the conditions of phimosis and paraphimosis.

Embodiments of the invention provide a device for manipulation of a foreskin of a male user. Such device includes (a) a protective cup dimensioned to be affixed to an underwear of the male user to accommodate and cover at least a front portion of an uncircumcised penis of the user to prevent contact between the at least front portion and an object outside the cup; and (b) a flexible foreskin stopper unit that contains a flexible central body (dimensioned to be positioned in contact with at least such front portion of the penis and having a first outer dimension) and first and second arm extensions protruding from the flexible central body in substantially opposite directions. Here, the protective cup is configured to have the stopper unit removably and repositionally affixed to and inside the protective cup via cooperation of the first and second arm extensions with the protective cup.

At least one of the first and second arm extensions may contain multiple tabs or protrusions extending transversely from a corresponding arm extension, while the protective cup may contains multiple openings throughout a wall thereof (to be cooperated with such protrusions in operation of the device). Additionally, the protective cup is configured to substantially prevent an occurrence of a disconnect (in absence of external input) between the first and second arm extensions—that have been pulled respectively through first and second openings to connect the stopper unit to the cup—by keeping the first and second arm extensions under tension. Additionally, or in the alternative, the flexible central body of the stopper unit may be configured to stretch along an axis of an arm extension when the first and second arm extensions are removably and repositionally affixed to the protective cup.

When the protective cup is equipped multiple openings through a wall of the cup, the first outer dimension may be made smaller than a maximum diameter of a glans of the penis such that, when the flexible central body is brought in contact with a tip of the penis and foreskin covering the tip and when the first and second arm extensions are pulled respectively through first and second openings from inside the protective cup and affixed to the cup in tensioned contact with the cup, the flexible central body is forced to apply at least outwardly radial pressure to the foreskin along an axis of a chosen arm extension. Alternatively, or in addition, the pressure applied by the flexible central body to the foreskin in this case may include a second pressure applied to the foreskin in a direction of a body of the user.

In a specific case, when the flexible central body of the foreskin stopper unit includes a ring and when the protective cup includes multiple openings as mentioned above, the foreskin stopper unit may be configured such that one of the following conditions is satisfied: (a) the ring diameter is smaller than a maximum diameter of a glans of the penis such that, when the ring is brought in contact with a tip of the penis and when the first and second arm extensions are pulled respectively through first and second openings from inside the protective cup and affixed to the cup under tension the ring applies at least outwardly radial pressure to the foreskin along an axis of a chosen arm extension; and (b) the ring is dimensioned such that, when the ring is installed onto and in contact with a shaft of the penis having the glans and mucosal membranes exposed and when the first and second arm extensions are pulled respectively through the first and second openings from inside the protective cup and affixed to the in tensioned contact therewith, the ring applies to the foreskin a force directed along the shaft.

In every and/or any of these implementations, the foreskin stopper unit may include an elastic material configured to maintain the penis under radial pressure when the ring is in contact with the shaft. Alternatively, or in addition, the foreskin stopper unit may include multiple radially extending finger-like protrusions on an inner surface of the ring component.

Embodiments of the invention further provide a method for manipulation of the foreskin with the use of the above-mentioned device. Such process of manipulation includes at least a step of positioning the foreskin stopper unit inside the protective cup of the underwear worn by the user with the first and second arm extensions being removably affixed to the protective cup; a step of bringing the flexible central body in contact with either (i) the glans and an edge of the foreskin that covers a portion of the glans, or (ii) a shaft of the penis having the glans and mucosal membranes exposed (depending on the specifics of implementation of the flexible central body of the foreskin stopper unit); and a step of applying a first pressure to the foreskin directed substantially radially with respect to the shaft by stretching the first and second arm extensions affixed to the protective cup. In at least one implementation, the process may additionally include a step of applying a second pressure to the foreskin directed substantially along the shaft.

In a specific case (when the flexible central body component includes a ring), and when a ring diameter is smaller than a maximum diameter of a glans of the penis, the step of bringing may include bringing the ring in contact with a tip of the penis to apply the first pressure under tension created by the stretching of the first and second arm extensions. Alternatively, when the ring is dimensioned to be installed onto and in contact with a shaft of the penis having the glans and mucosal membranes exposed, the step of bringing may include applying the first pressure to the foreskin and the shaft under such tension. Alternatively, or in addition, the method may additional include applying to the foreskin a force directed along the shaft with the ring being in contact with the foreskin,

BRIEF DESCRIPTIONS OF THE DRAWINGS

FIG. 1 is a schematic side view of a penis.

FIG. 2 is an isometric view of the clip shown in FIG. 3.

FIG. 3 is an isometric view of two clips retracting foreskin.

FIGS. 4, 5 provide an isometric view of an embodiment utilizing two clips connected with a perforated hollow cylinder and cooperation of such embodiment with the shaft of the penis in operation.

FIGS. 6, 7 provide an isometric view of an embodiment utilizing two clips connected with a hollow mesh cylindrical component and cooperation of such embodiment with the shaft during use.

FIGS. 8A, 8B illustrate in perspective views two generally-differently dimensioned hollow-cylindrical components of a related embodiment of the invention, which in operation are disposed co-axially with respect to one another.

FIGS. 9, 10, 11, and 12 provide schematic illustration to the process of using the embodiment that incorporates the components of FIGS. 8A and 8B.

Figure 10:
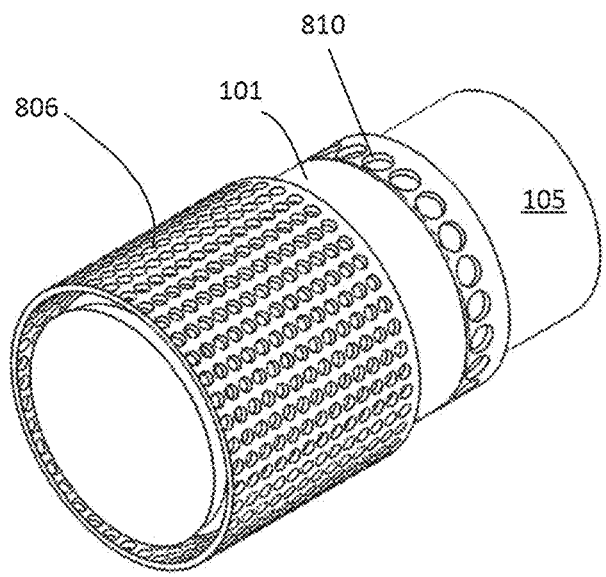
Figure 11:
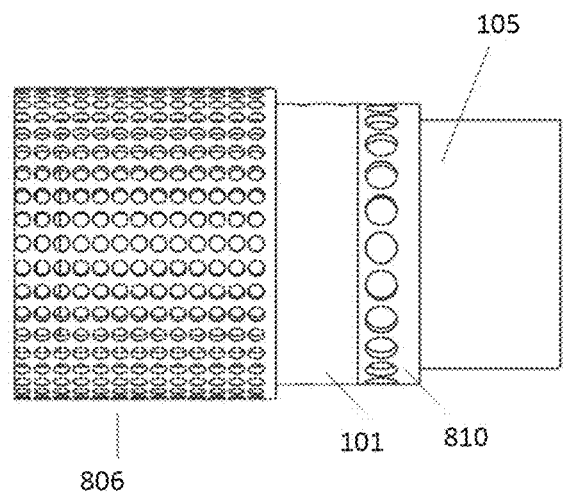
Figure 12:
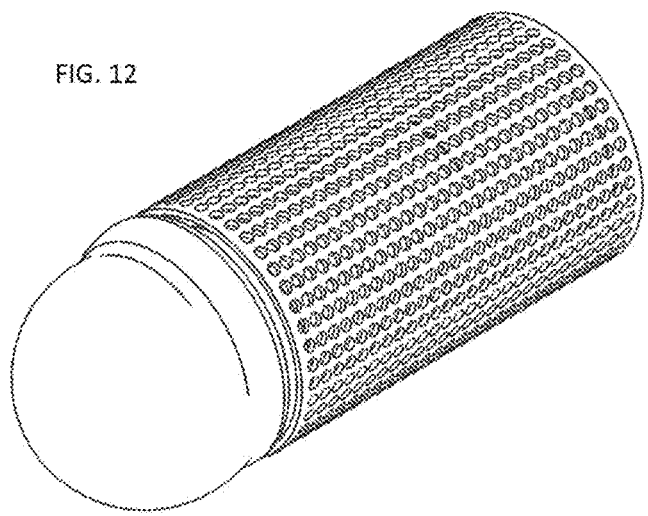
Figure 13:
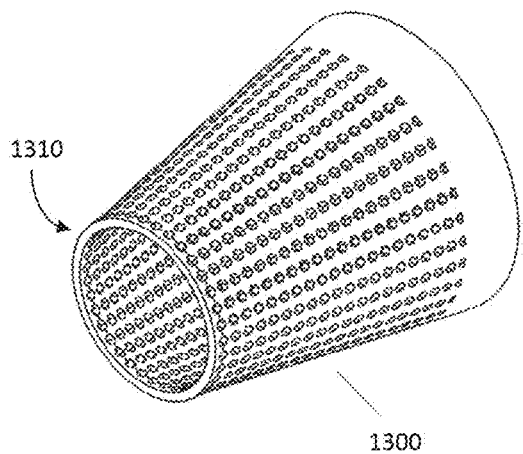
Figure 14:
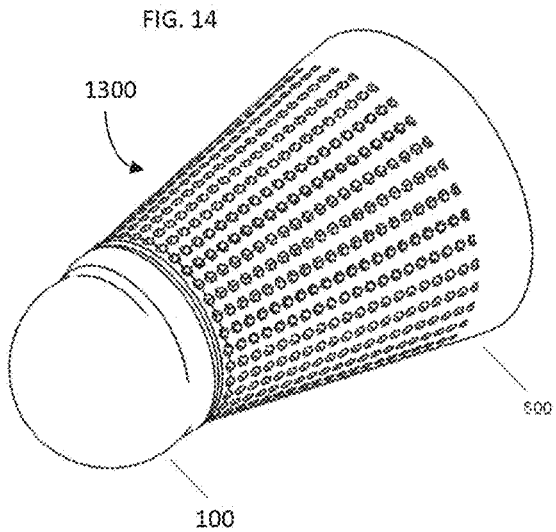

FIGS. 13, 14 illustrate a related embodiment of the device of the invention utilizing a hollow conical component and the cooperation thereof with the shaft of the penis in use.

Figure 15:
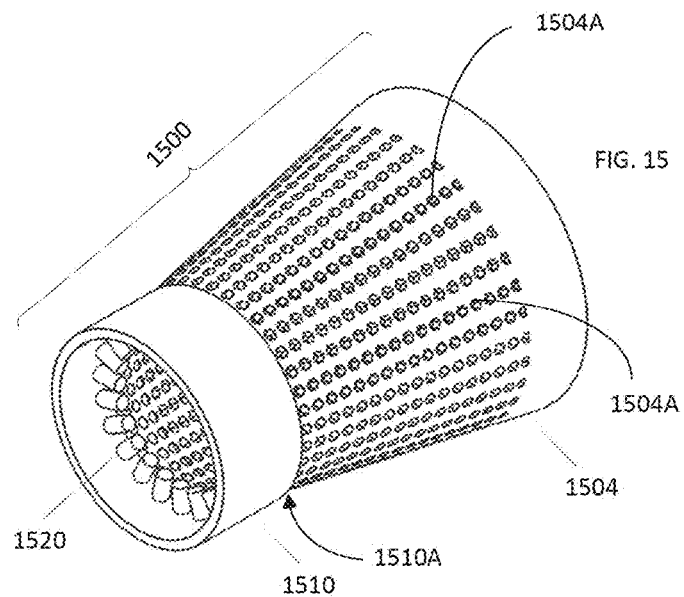
Figure 16:
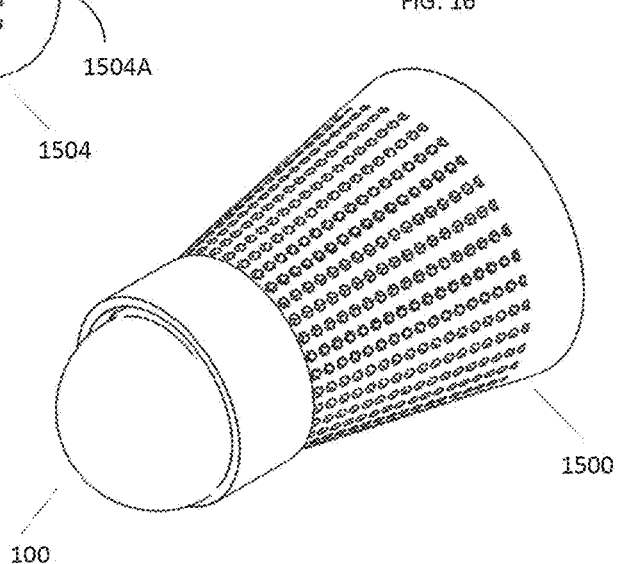

FIGS. 15, 16 provide illustrations of yet another embodiment that contains a hollow perforated conical component (a tapered component) juxtaposed with a hollow cylindrical unit and equipped with tactile flanges, as well as the cooperation of this embodiment with the shaft of the penis.

Figure 17:
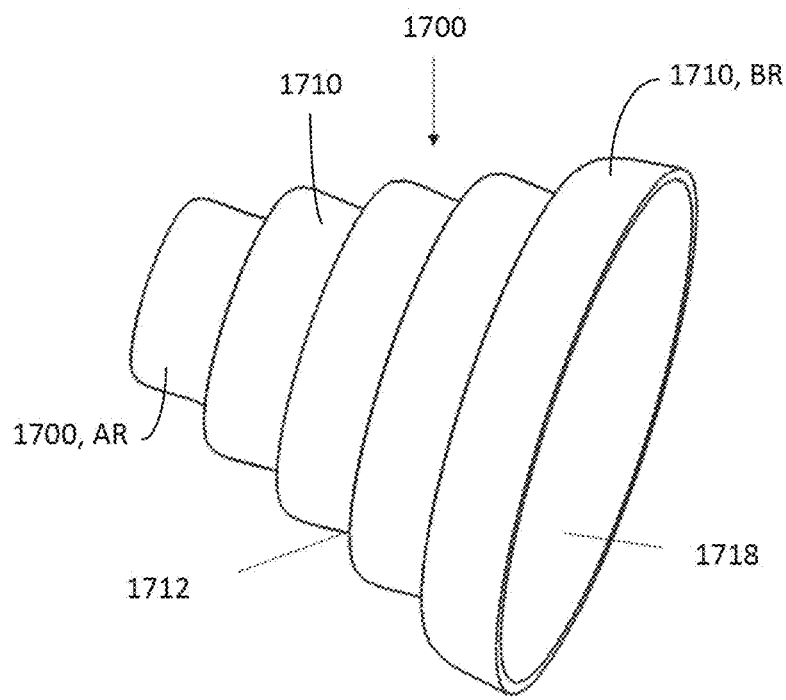
Figure 18:
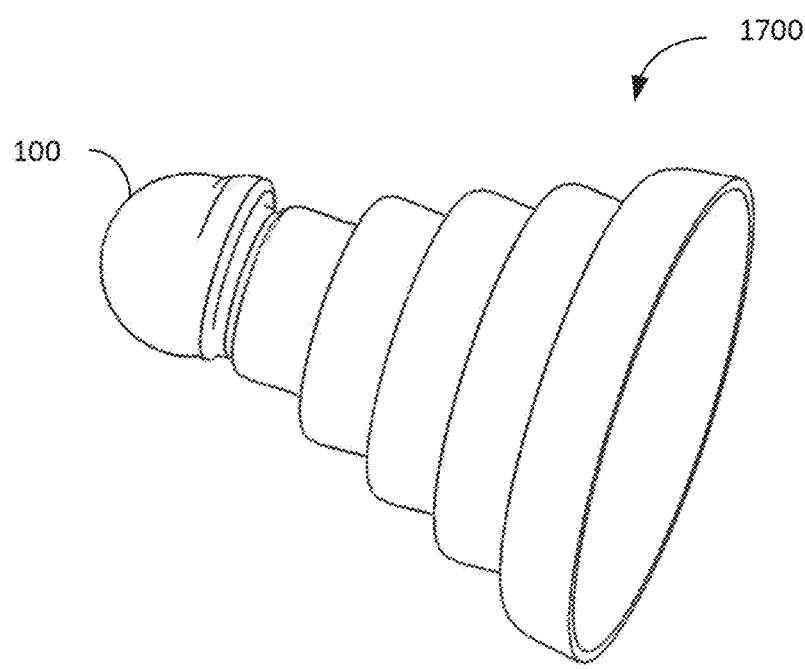

FIGS. 17, 18 provide perspective-view illustrations to yet another related embodiment of the device of the invention.

FIGS. 19, 20 provide an isometric view of a manual retraction device configured according to the idea of the invention, and a retracting as part of such device, respectively.

Figure 21:
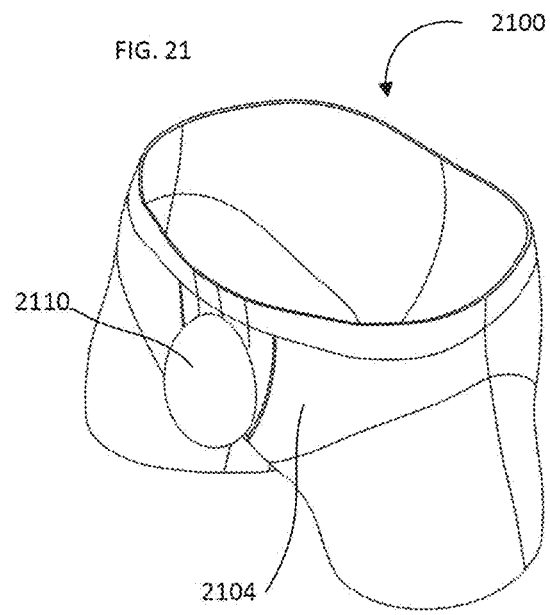
Figure 22:
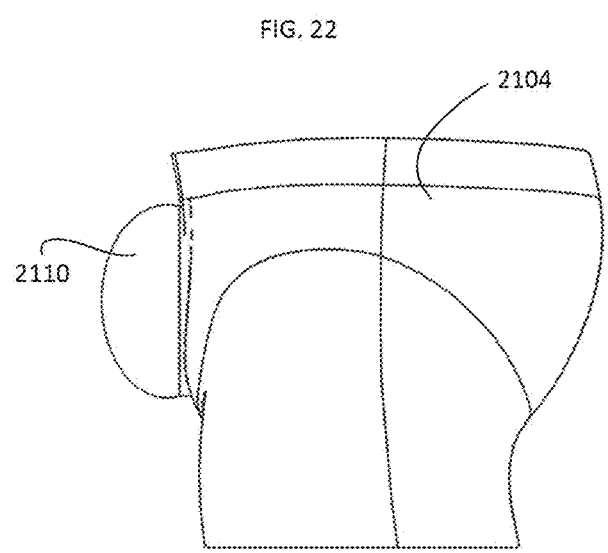

FIGS. 21, 22 illustrate an undergarment with an optional undergarment component that can be configured for use with at least some of embodiments of the invention.

FIGS. 23, 24, 25, 26, and 27 schematically illustrate yet another related embodiment of the invention (used in practice with the undergarment of FIGS. 21, 22) and employing a pneumatic ring element.

Figure 28:
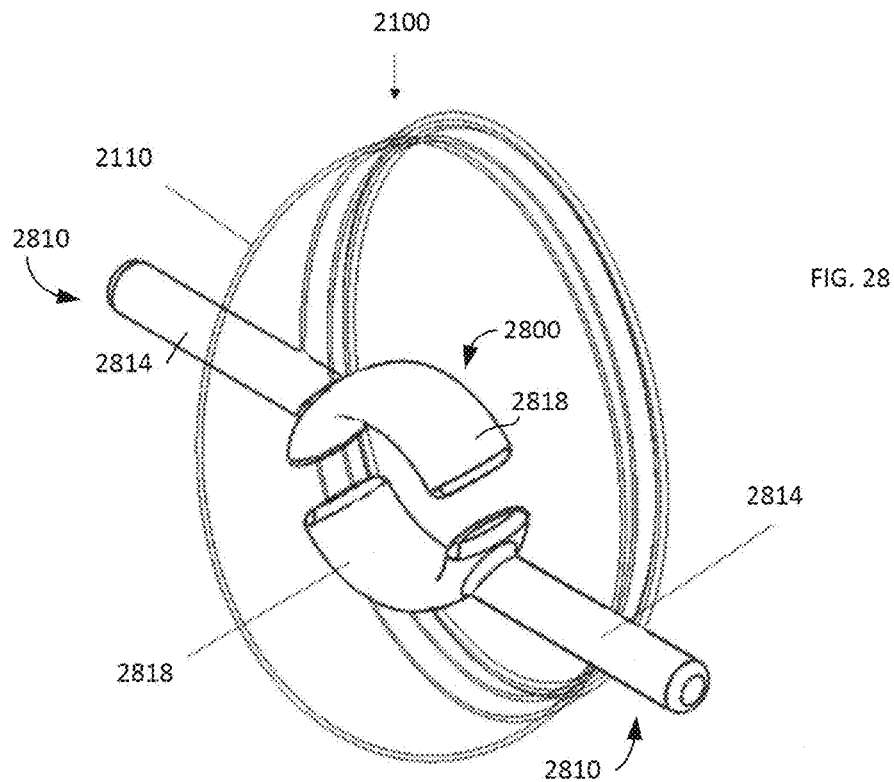
Figure 29:
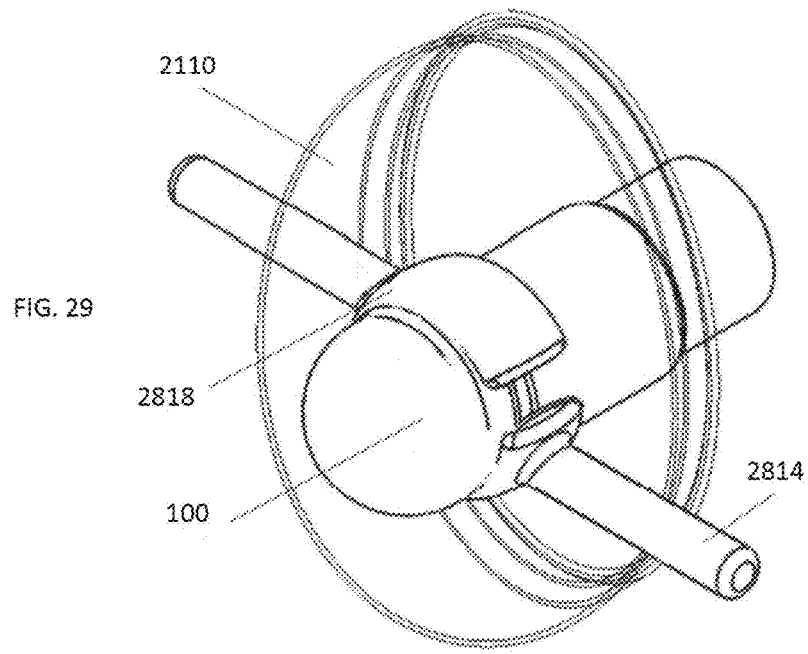

FIGS. 28, 29 illustrate in isometric view a finger-like projection retraction embodiment of the device mounted in the protective cup of the undergarment, by itself and mounted on the shaft of the penis, respectively.

Figure 30:
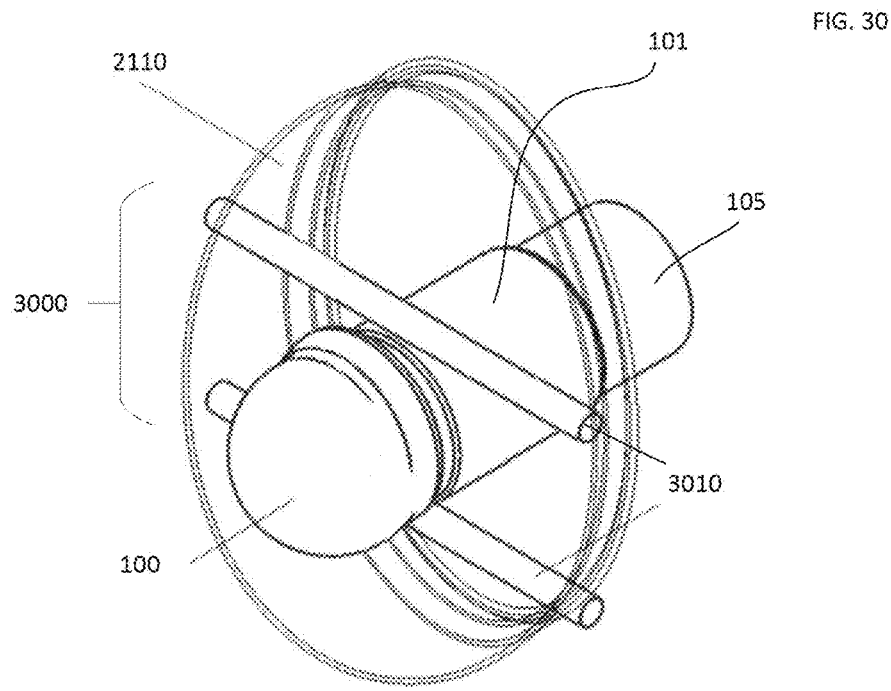
Figure 31:
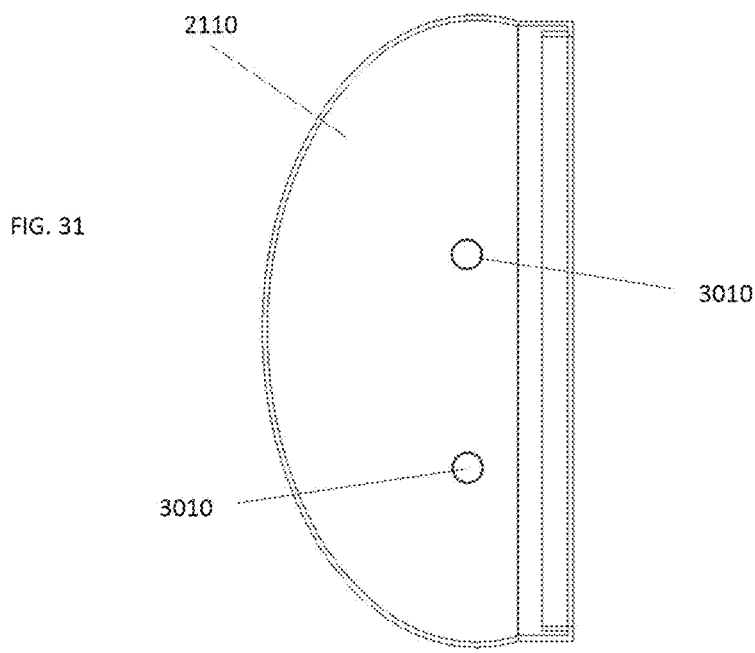

FIGS. 30, 31 illustrate the structure and use of another related embodiment of the invention.

Figure 32:
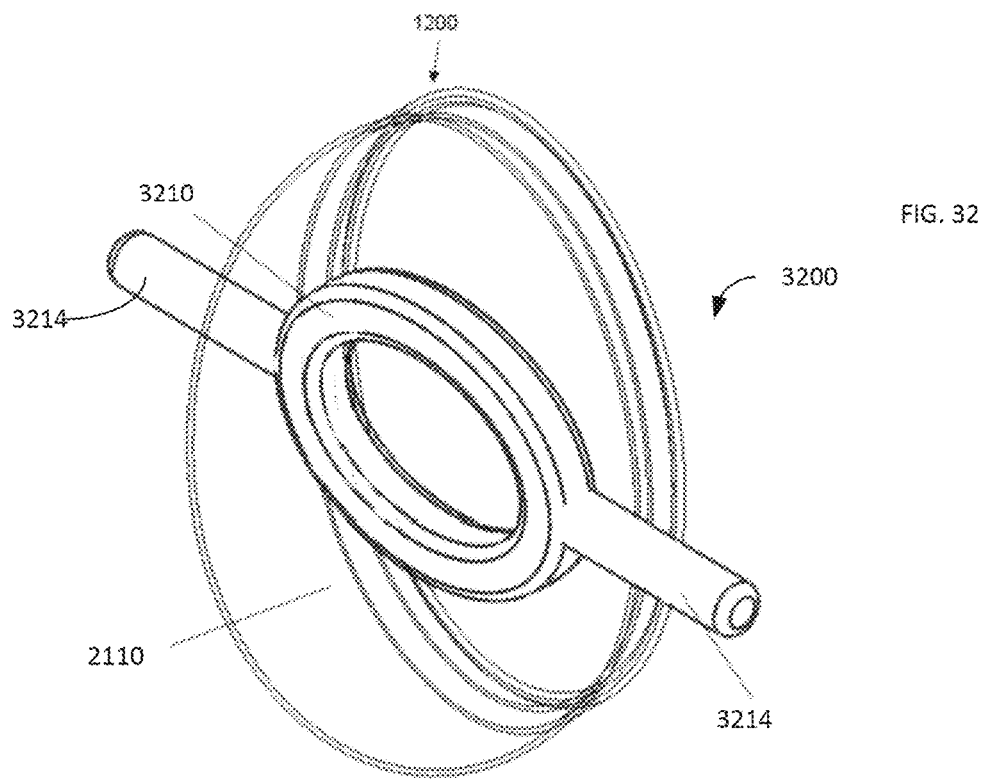
Figure 33:
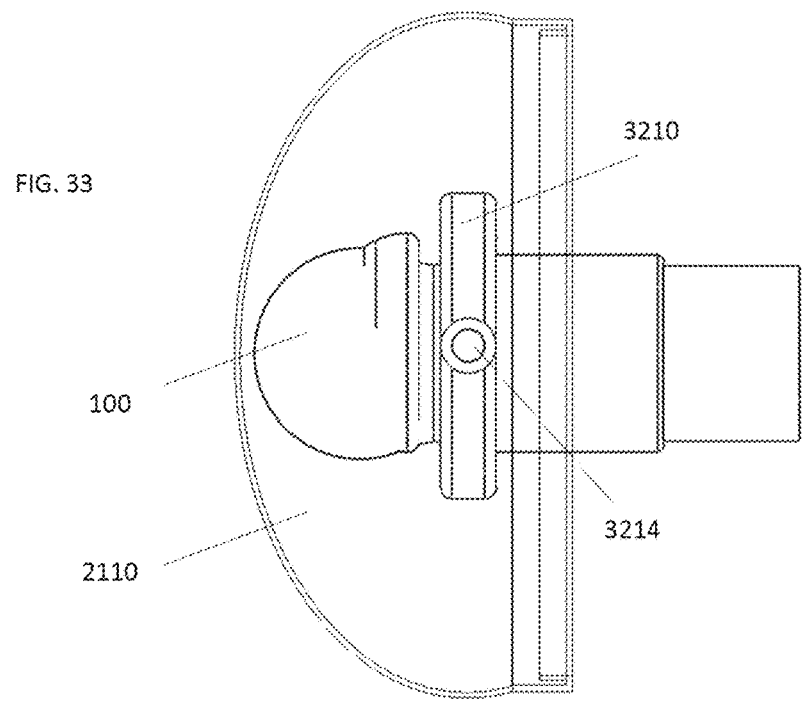

FIGS. 32, 33 schematically illustrate the structure and use of yet another related embodiment of the invention.

Figures 34A, 34B:
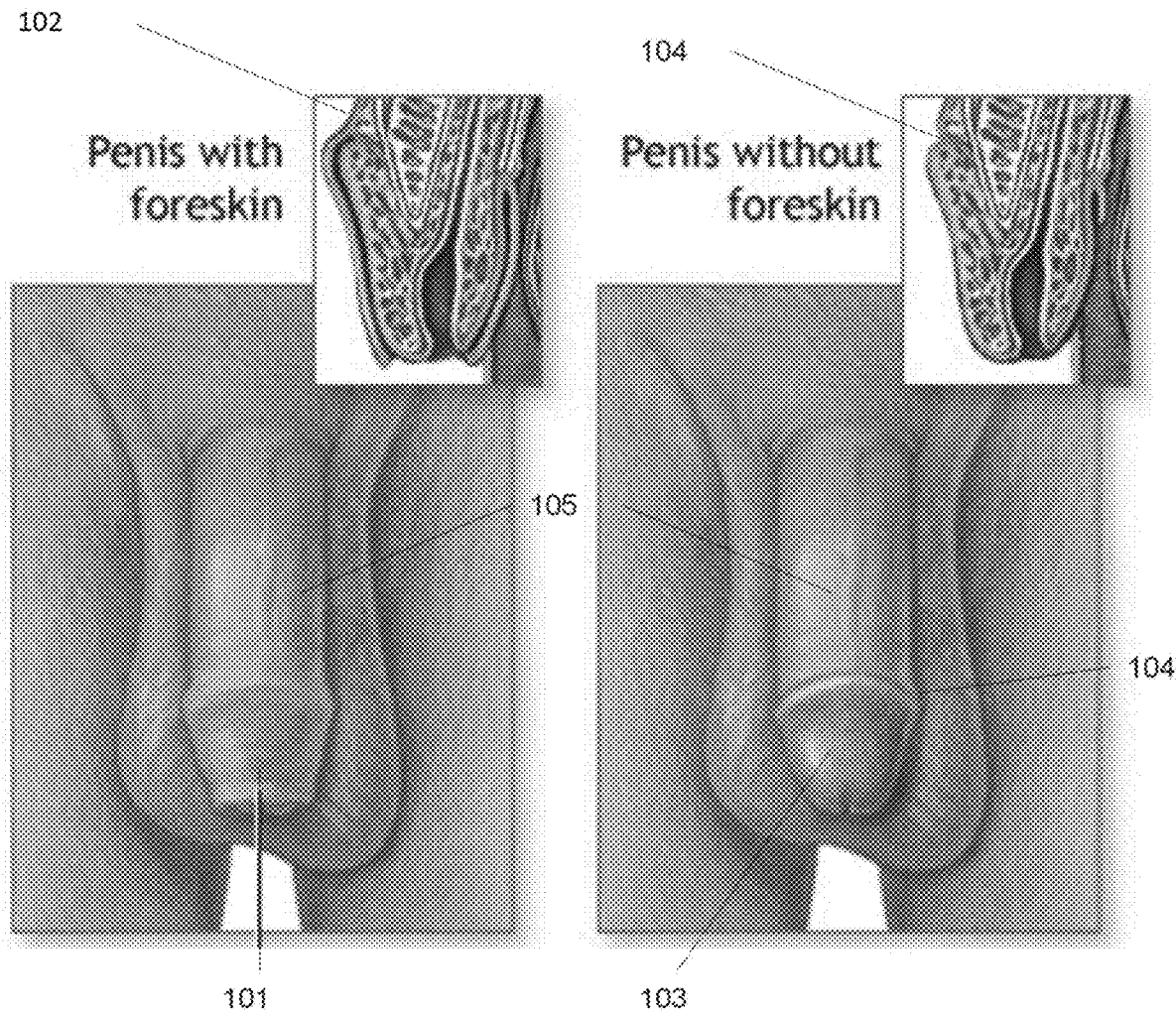

FIGS. 34A, 34B provide front views of the non-circumcised penis and circumcised penis, respectively, with identification of portions thereof relevant to the description of embodiments of the invention.

Figure 35A:
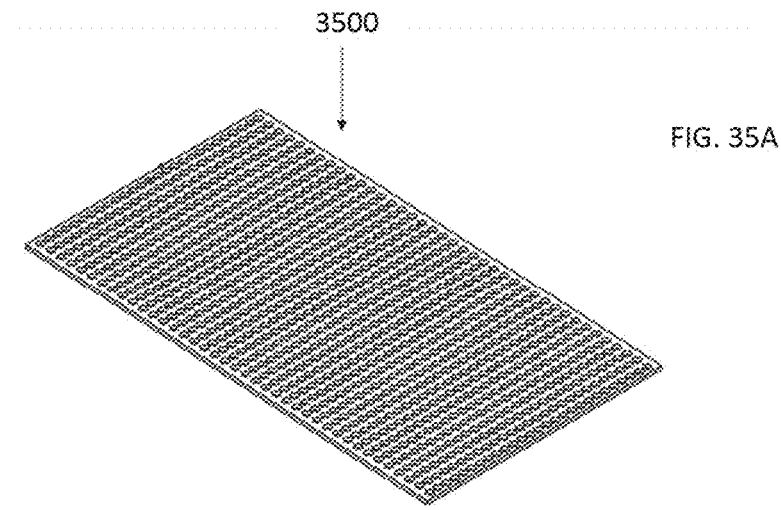
Figure 35B:
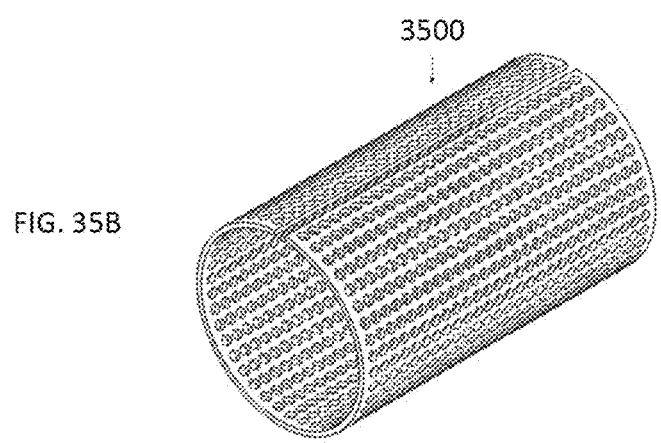
Figure 35C:
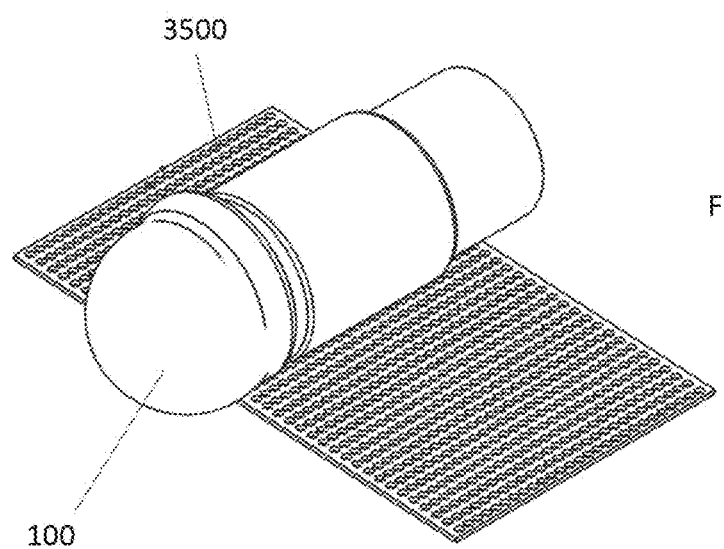

FIGS. 35A, 35B, 35C provide different views of an embodiment based on a flexible sheet fastener.

Figure 36:
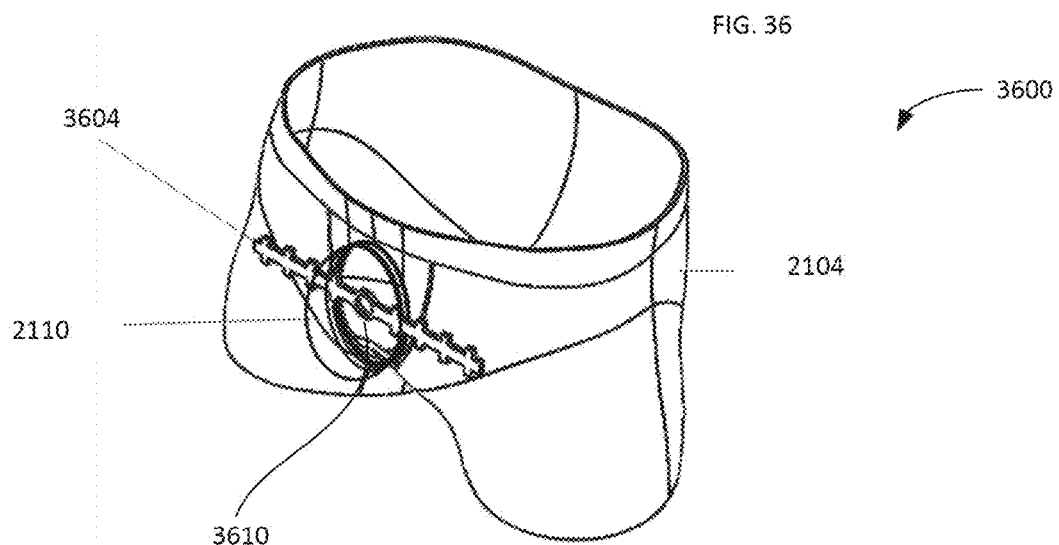
Figure 37:
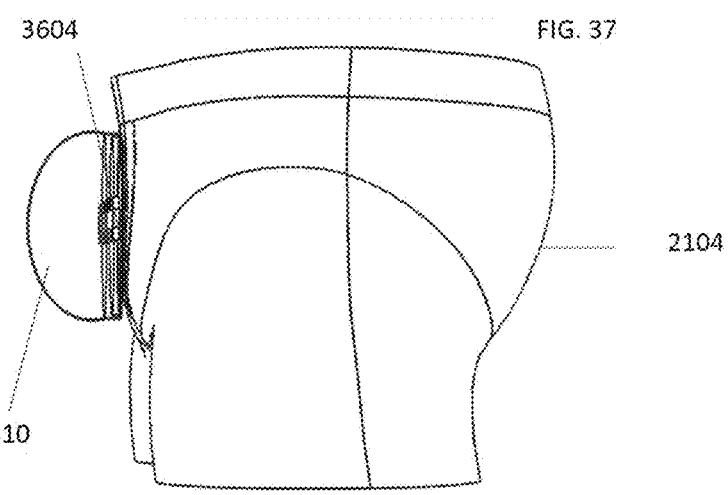
Figure 38:
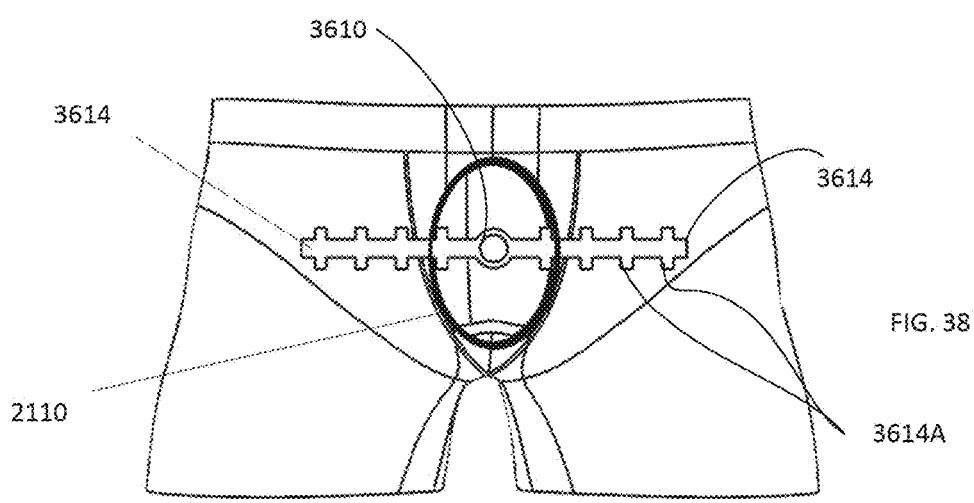

FIGS. 36, 37, and 38 illustrate schematically the structure and use of yet another related embodiment of the invention.

FIGS. 39A, 39B, 40, 41A, 41B provide additional illustrations of embodiment(s) of the device configure to be used for treatment of phimosis/paraphimosis.

DETAILED DESCRIPTION OF THE DRAWINGS

FIG. 1 schematically illustrates in a side view a model of a penis 100 used to describe embodiments of the penile foreskin retractor and to illustrate the method of wearing the penile foreskin retractor on the penis. Here, inverted foreskin in indicated as 101, the point/area of attachment of foreskin to penis as 102, 103 denotes the glans of penis with 104 identifying the neck of glans, while the penis shaft with penile skin is labeled as 105. The numeral 106 identifies the mucosal membranes on the inverted foreskin 101. See also FIGS. 34A, 34B for additional illustrations showing additional images to enhance the understanding the anatomy related to foreskin.

An embodiment of a clip 200 configured to retract and maintain foreskin retraction when cooperated with the penis 100 (typically, as parts of an embodiment of the overall device) is presented in an isometric view in FIG. 2. The clip is shaped as an arched coil 200A with ends 200B protruding away from the venter of the coil 200A, thereby formatting the clip 200 as (a portion of) a torsion spring. FIG. 3 illustrates a constricting (spring-like) cooperation of each of multiple clips 200 fitted with the body of the penis 100. In operation, the user manually retracts the foreskin towards the body exposing the glans 103, then securing a clip 200 to the neck of glans 104; another clip 200 may be worn on the shaft on top of the retracted foreskin, as shown in FIG. 3. The clips 200 can be appropriately configured from materials that provide magnetic repulsion of one clip from another, to maintain a desired distance between the clips disposed apart from one another, to maintain a desired distance therebetween and therefore maintaining the retraction of the foreskin. In such a case, the front clip that is secured immediately behind the penis glans 103 may push the second ring toward the body using magnetic repulsion forces.

In a related implementation, multiple clips 200 are used not by themselves but in cooperation with a tube-like and generally cylindrical element shown in the specific embodiment of FIGS. 4, 5 as a porous or perforated hollow cylinder 400 (or a hollow cylinder the wall of which contains multiple openings 404 therethrough, optionally both along the length of the cylinder 400, arranged in multiple columns, and circumferentially, arranged in multiple rows). In one case, the openings 404 are formed by appropriately perforating the sheet of material forming the wall of the cylinder 400. Depending on a particular implementation, the aggregate area defined by the openings 404 is at least 30% or more, 50% or more, or even 70% or more of an area of the outer surface of the wall of the cylinder 400. Notably, the areal density of the holes/openings 404 may be higher on that portion of the cylinder that retracts and overlaps the retracted foreskin (that is, in the portion of the cylindrical element 400 that in operation is installed proximal to the body of the user). In one implementation, at least one of the multiple clip 200 (as shown—the one positioned distally with respect to the glans 103) is cooperated with the embodiment 400 by passing the ends 200B of the clip through two corresponding throughout openings 404 that are approximately opposing one another. In a related implementation (not shown), at least one of the multiple clips is disposed above and around the cylinder 404.

In operation, the user pulls the foreskin towards the shaft to expose penis head (glans) 103 and then inserts the penis into a proximal clip 200 cooperated with the cylinder 400 and through the 201, see FIG. 5. Furthermore, the user may also pull the porous/perforated hollow cylinder 404 closer to the body until the edge of the cylinder is aligned with the neck of glans 104 (behind the head of the penis). Therefore, another (front) clip 200 is secured on the penis neck spring action of the clip and prevents the cylinder 404 from sliding towards and onto the penis glans 103 thereby keeps the retracted foreskin in place on the shaft of the penis under the cylinder 400 and away from the penis head; FIG. 5.

When none of the clips 200 is embedded into or passed through the structure of the cylinder 400, the position first and second clips 200 (with respect to the body of the cylinder 400) may utilize shape-memory properties of the materials used in the porous cylinder.

In this case, the used material may be chosen (such as nitinol (nickel-titanium), PTFE, Spandex, Silicone, Polyurethane, to name just a few) to have appropriate elastic properties to hold on to the penis and change the geometry of the cylinder (diameter, length) as the penis changes its shape and size. The elasticity and pressure exerted on the penis by such porous cylinder portion holds the device in place and keep the skin retracted while not interfering with blood circulation or cause discomfort to the user.

In an embodiment 600 of FIGS. 6, 7 (which is related to the embodiment 400), the cylindrical portion is shown formed from a mesh or netted material with multiple mesh openings 604.

In reference to FIGS. 8A, 8B, 9, 10, 11, 12, an embodiment utilizing a cylindrical element (such as a porous cylinder 400, or a mesh cylinder 600) may employ multiple of such cylindrical elements of different diameters cooperated co-axially with one another. Here, the cylinder 806 of FIG. 8A is larger both in diameter and in length as compared to the cylinder 810 of FIG. 8B. The method of foreskin retraction utilizing the embodiment employing both cylinders requires the user first to insert the smaller diameter cylinder 810 over the penis. The user then pulls the foreskin 101 towards the shaft to expose penis head (glans) 103 and over the cylinder 810, as is schematically illustrated in FIG. 9. Once the foreskin is positioned over the cylinder 810, the penis is inserted into the cylinder 806 until it reaches the neck of glans 104 (see sequence of FIGS. 10, 11, 12), thereby sandwiching the foreskin 101 between the cylinders 810 and 806. The cylinders 806, 810 may be made of materials that may have shape memory properties, magnetic elements, or other means to create the necessary force required for sustained foreskin retraction and inversion. As shown, the edge of the device may abut to the glans 103 of the penis to create a reaction force needed for the foreskin retraction and inversion.

In at least one case at least one of the cylindrical components (e.g., 400, 600, 806 etc.) may be spatially-tapered—as schematically illustrated in the case of embodiment 1300 of FIGS. 13, 14—to form a substantially-conical component the front (narrow) end 1310 of which is in practice disposed to abut the glans 103 to enhance the attachment to the penis.

Alternatively or in addition, either the cylindrical or the conical component of the device (whether it is formatted as a "porous" component that contains a multiplicity of throughout openings, or a substantially spatially-uninterrupted wall, or a wall made of a mesh) may be complemented with finger-like protrusions disposed on the inner side of the corresponding cylinder (or cone) to aid the action of retracting the foreskin by providing multiple touch points instead of a circumferential edge or surface contact between the cylindrical (or conical) component of the device and the foreskin while, at the same time, increasing comfort of the wearer during the use of the device. As shown in FIGS. 15, 16, for example, the embodiment 1500 includes a substantially conical element 1504 containing multiple throughout openings or "pours" 1504A and providing a taper from the first end of it (disposed in operation closer to the body of the user) to the second or front end of it (disposed in operation at the glans 103) and the spatially-uninterrupted cylindrical component or ring 1510. For the convenience and comfort of use of the device, the diameter of the cylindrical component 1510 and that of the front end of the conical porous component 1504 are substantially equal to one another, such that the components 1504, 1510 are merging one into another along the edge of the cylinder 1510. In one implementation, such merging is structured to be tangential to ensure that at least one of the outer and inner surfaces of the embodiment 1500 in the immediate vicinity of the edge 1510A is differentiable. As is schematically illustrated in FIG. 15, on the inner surface of the embodiment 1500 the multiplicity of finger-like protrusions 1520 (formed in one case from polymeric material) are disposed in a circumferential manner around the line of the edge 1510A. As illustrated in FIG. 16, the ring element 1510 of the embodiment 1500, when positioned over the penis, may be at least partially covering the glans 103. Understandably, any of the previously-discussed implementations in which a cylindrical component is used (e.g., 600) can also be complemented with the protrusions similar to protrusions 1520—in this case, the protrusions may be formed on the inner surface of the corresponding cylinder substantially close to or at the edge of it. As a non-limiting example, finger-like protrusion geometry may be cylindrical, conical, knurled, and/or dimpled. Lengths of these protrusions may be from about 1 mm to about 15 mm. Thickness or diameter may be in the range of 1 mm to 10 mm. Number of protrusions will depend on the diameter of the component 1510A, but separations of protrusions along the circumference is preferably equidistant and approximately equal to half the diameter of a protrusion. The practical reason for this formulaic distribution of protrusions is to grip the foreskin and create an inversion of the foreskin as the penis is introduced through the device. Protrusions will then act as the stopper elements to hold inverted foreskin in place.

Referring now to FIGS. 17, 18, in at least one embodiment 1700, the retraction device of the invention may be configured as a baffled hollow device—the one employing multiple rigid ring-like hollow elements 1710 of different diameters connected with each other using connecting sections 1712 made of flexible polymers material(s). The device's overall shape in this case may be a conical spring with the base ring BR in operation positioned closer to the body of the wearer. In this case, understandably, the base ring BR is dimensioned to have a bigger diameter than the immediately-neighboring ring, and the diameters of the remaining rings 1710 are reduced with the apex ring AR having the smallest diameter of them all. Due to the presence of the flexible connecting sections 1712, the device 1700 is collapsible upon itself, such that is a "folded" or "collapsed" state at least one of the rings 1710 having a smaller diameter is positioned inside the ring 1710 that has a larger diameter. The collapsible and foldable section of the baffled retraction device 1700 may allow the device to move with the changing size and shape of the penis with a desired force of retraction to provide a reaction force needed for foreskin retraction and inversion. To install the device, the user pulls the foreskin towards the shaft to expose penis head (glans) 103 and then inserts the penis into baffled retraction device 1700 from the base ring BR (as shown by numeral 1718) toward the apex ring AR. The base ring BR may then be secured on the undergarment (as discussed in more detail below) to hold position while the apex ring remains in contact with the foreskin to hold the retracted foreskin in place as shown in FIG. 18.

In yet another related embodiment, the embodiment 1900 of the foreskin retraction device includes a cylindrical component 1910 (shown in FIG. 19 to be of a porous variety that is juxtaposed with a retractor unit 1912. The retractor unit 1912 contains a ring 1914 equipped with a handle or button 1918. When assembled together, the ring 1914 of length or width L1 is disposed inside of and substantially coaxially with the cylindrical component 1910 while the neck of the handle 1914 is passed through a slot or throughout groove 1920 (formed in the body of the cylindrical component 1910 and shown in FIG. 19 to have a length L2>L1). The geometries of the components 1910, 1914 are judiciously chosen to ensure that the ring 1914 smoothly slides inside the cylinder 1910 in contact with the inner surface of the cylinder 1910 and without mechanical rattling when the handle 1918 is moved along the slot 1920. The material of the ring 1914 is chosen to maintain connection with the foreskin and apply such desired force.

In operation, the device 1900 is disposed around the penis with the ring 1914 abutting the glans 103 and the handle 1914 in close proximity to the glans. In particular, the user pulls the foreskin towards the shaft to expose penis head (glans) 103 and then inserts the penis into the retracting ring 1914 through the cylinder 1910. The user may also pull the cylinder 1910 until it reaches the neck of glans 103 (behind the head of the penis). The ring 1914 is then secured on inverted foreskin using ring elasticity. The design allows the user to adjust retraction force as desired: the retractive handle 1918 is configured to allow the user to adjust the force when moving the ring 1912 backwards to create a force required for skin retraction and inversion. The ring 1914 may be use the cylinder 1910 as a moving rail and a locking feature. In some embodiments of the device, the retracting part 1912 may retract the foreskin as the user wears the device and in other embodiments. The user must retract the foreskin manually before wearing the device. (Additionally, as discussed below, the embodiment 1900 may be anchored to accessories worn around the body such as an undergarment to provide a reaction force needed for foreskin retraction and inversion.)

Substantially any embodiment of the retraction device may be in practice anchored to accessories 2100 shown in FIGS. 21, 22 worn around the body of the user (such as an undergarment 2104) to provide a reaction force needed for foreskin retraction and inversion. The undergarment shown in FIGS. 21, 22, may also have judiciously dimensioned constituent component(s)—for example, a component 2110 (shown to be similar to an athletic cup, or alternatively a baffled retraction device 1700 already discussed above) configured to serve as a protective shield for the exposed, sensitive penile skin from surrounding objects (e.g. clothing) and/or to be used simultaneously for retracting the foreskin. When the constituent component 2110 is configured as a protective cup, it may also be used as a base or support for multiple foreskin-retraction methods.

Figure 26:
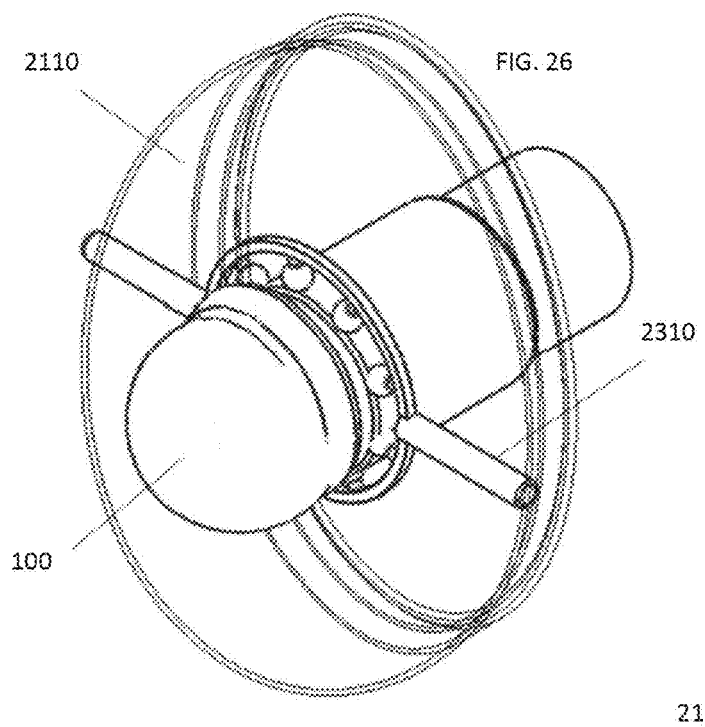
Figure 27:
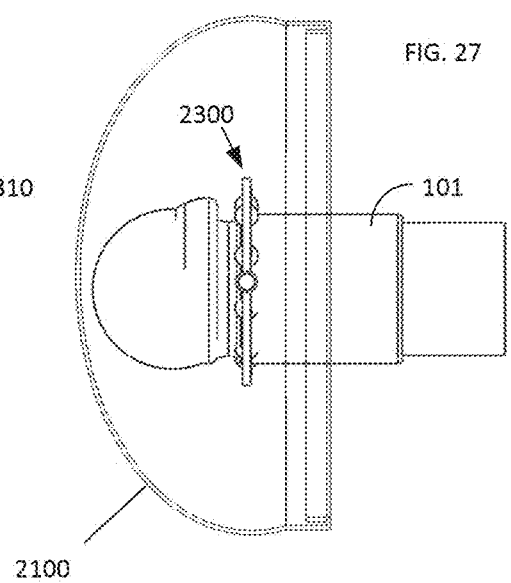
Figure 23:
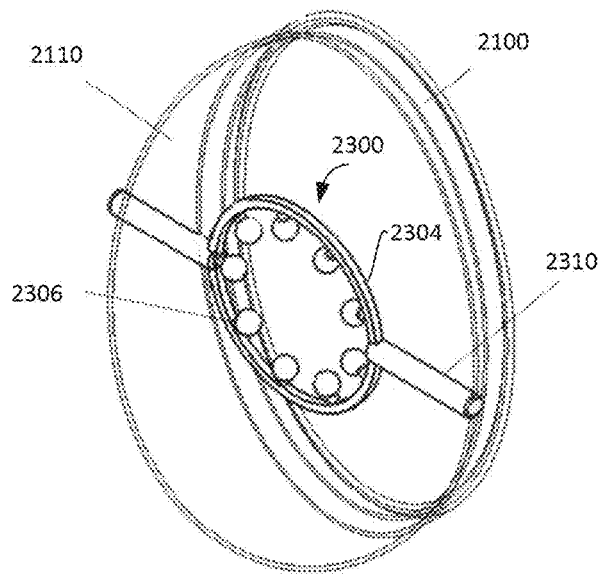
Figure 24:
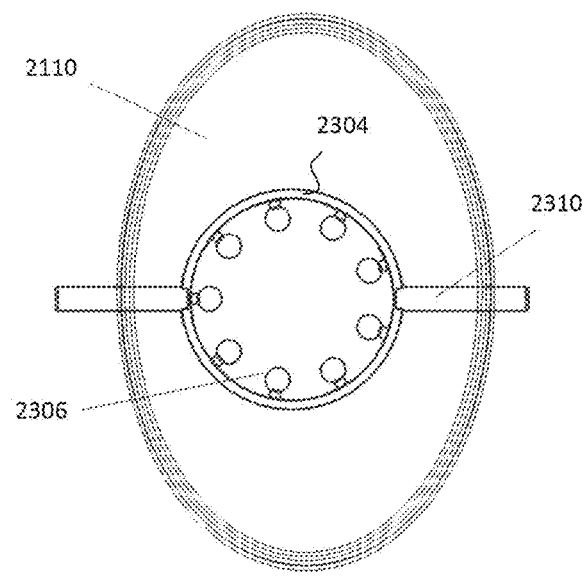
Figure 25:
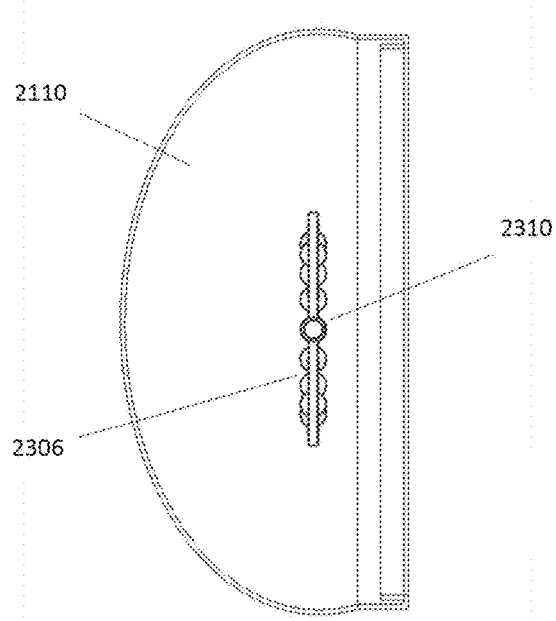

Furthermore, auxiliary units may be used to either be operated independently to retract and invert the foreskin or complement another embodiment of the retractive device. For example, as schematically illustrated in FIGS. 23, 24, 25, 26, and 27 the pneumatic ring-based device 2300 may be used to adjust the pressure applied on the penis to keep the retracted skin in place. The pneumatically-controlled outer circumferential cylinder or ring-like element 2304 for radial grip to the penis allows the user to adjust the pressure as desired, while the rod-like or tubular arms 2310 extending from the ring 2304 may in operation be affixed in/juxtaposed with at least one opening (not shown) formed in a protective cup 2110, for example. In one specific implementation, the pneumatic ring 2304 may use a self-regulating mechanism such as at least one radially-pointing extensions dimensioned as finger-like protrusions (configured, for example, as balloons or spheroids) 2306 on an inner surface of the element 2304 to allow a leeway as the penis changes in size to thereby enhance comfort and ensure retracted foreskin remains in retracted position. The user pulls the foreskin towards the shaft to expose penis head (glans) 103, then inserts the penis into pneumatic ring device 2300 until reaches the neck of glans 103 or the inverted foreskin. Then the device 2300 is secured in place with the use of the accessories 2100 (and optionally within the protection element 2110), as shown in FIGS. 26, 27 (here, the openings in the element 2110 through which supporting the arms 2310 are pulled are not shown for simplicity of illustration).

Yet another alternative arrangement of the foreskin retraction and inversion device 2800 is shown in FIGS. 28, 29, in combination with the accessor(ies) 2100, 2110. Here, the finger like projection contraption 2800 is shown to utilize two flexible arms 2810, each containing an extension element 2814 ending on one side with a respective arched element 2818 (which, as a pair are facing each other with concavities) while another side—the element 2814—being attached/fixed to the undergarment 2100/accessory 2110. Each of the arched elements 2818 can be thought of as a section of a ring, and the overall structure is dimensioned such as to accommodate and follow the change in the size and shape of the penis when such change occurs. The side of the arm 2810 containing the arched element 2818 may be made of soft material judiciously chosen to create a smooth contact with the penis 802. In operation, the two-arms are exerting pressure forces onto the penis 100 in two opposite directions (in reference to FIG. 29—along a vertical axis)) where the net of the two forces being negligible and substantially zero. The user pulls the foreskin towards the shaft to expose penis head (glans) 103, then places the arch-like projections 2818 on the opposite sides of the retracted and inverted foreskin against the glans 103 to use the glans 103 as anchoring location to maintain the arched elements 2818 (and, therefore, retracted and inverted foreskin underneath these elements) in substantially the same axial position along the shaft of the penis 100.

FIGS. 30, 31 aggregately provide illustrations to yet another related embodiment of the device 3000, that employs two rod-like or tube-like elements 3010 shown to cross the sagittal plane, FIG. 31, which in operation are to the undergarment (for example, passed through the openings in the supporting element 2110) at both ends. In operation, the elements 3010 tubes are disposed on and physically connected to the top and the bottom of the foreskin 101 to provide a reaction force needed for foreskin retraction and inversion as show in FIG. 30. Yet in another related embodiment 3200, device may include a cylindrical ring 3210 supported by the arm-extensions 3214. Depending on the nature of the material used for the ring 3210, this embodiment may be configured to have the capability to stretch and constrict as needed to result in a desired pressure to hold the foreskin in the retracted position without interrupting blood circulation or causing discomfort while the device is worn with the ring 3210 inserted over the shaft of the penis and the arms 3214 supported in the undergarment 2110 (for example, in the openings of the protective element 2110). The design may consist of composite materials, both by combining homogeneous materials and using multiple materials heterogeneously in tandem, to satisfy the desired application. In operation—especially when the undergarment cup 2110 is made deformable, the user can push the sides of the cup to dilate the vertical distance between the arm extensions for the purpose of repositioning the shaft of the penis longitudinally.

FIGS. 35A, 35B, 35C illustrate a flexible sheet fastener 3500 (FIG. 35A: in a flat state; FIG. 35B: in a curved state) A flexible sheet fastener 3500 can be made of composite materials consisting of elastic or inelastic materials to maintain a desired pressure on the foreskin capable of changing shape to be wrapped around the penis to hold the retracted foreskin in place. The fastener 3500 can hold the position around the penis (around which the fastener is wrapped after the foreskin has been retracted, for example) using Velcro, stapler pin, or button, for example, as shown in FIG. 35C.

Yet additional related implementation 3600 of the device for manipulation of the foreskin, schematically illustrated in FIGS. 36, 37, 38, includes a combination of the protective cup 2100 (that is dimensioned to be affixed to the underwear of the male user such as to cover at least a front portion of an uncircumcised penis to prevent contact between this front portion and an object outside the cup—for example, to prevent the sexual use) with the implementation 3604 of a flexible foreskin stopper unit that generally includes a flexible central body 3610 (shown in FIG. 36 in its specific implementation as a ring 3610) that is dimensioned to be positioned in contact with the at least front portion of the penis. The flexible central body 3610 is preferably integral with and is supported by the arm-extensions 3614 that are, in turn, are affixed in/supported by the components of the undergarment (for example, by the very protective cup 2110 through the openings in which the arms 3614 are pulled and secured as a result of tension in/stretching of the arms 3614 formed due to contact of the protrusions or tabs 3614A, extending from the arms 3614 in opposite directions, with a surface of the protective cup 2110). The protective cup is structured to have the stopper unit 3604 removably and repositionally affixed to and inside the protective cup via cooperation of the arms (or arm extensions) 3614 with the protective cup. The protective cup 2100 is configured to substantially prevent an occurrence of a disconnect, in absence of external input, between the first and second arm extensions 3614 (which have been pulled respectively through the openings in a wall of the cup 2100) by keeping the arm extensions 3614 under tension.

Figure 39A:
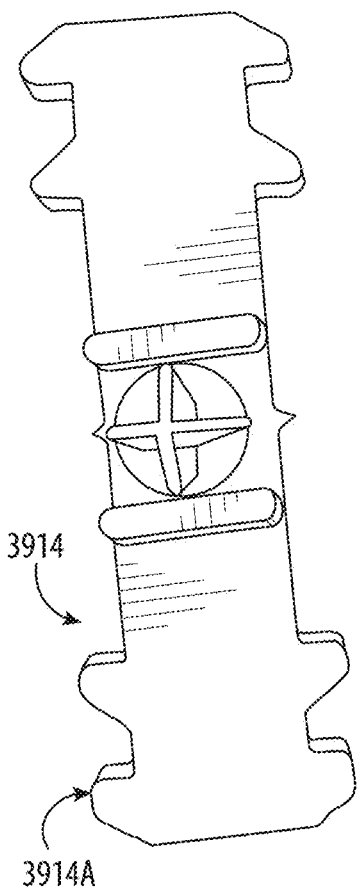
Figure 39B:
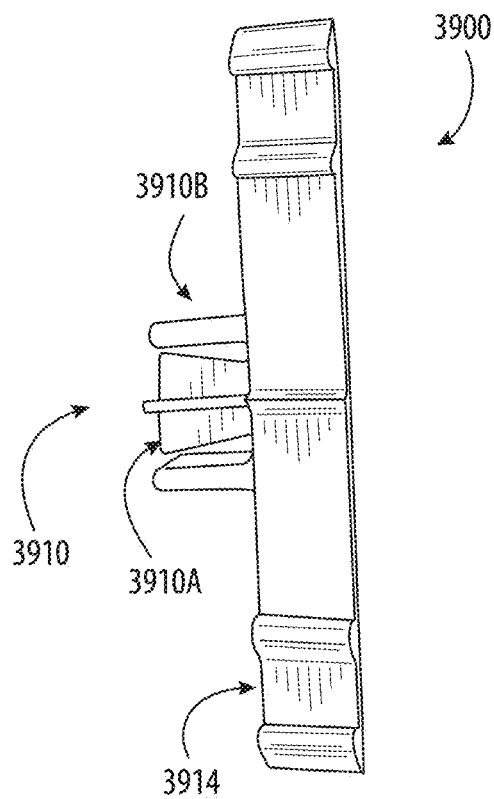
Figure 40:
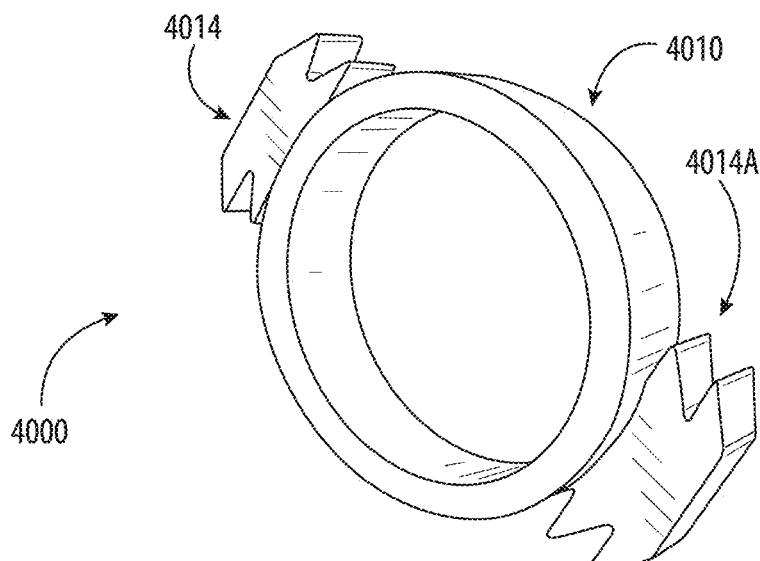

While FIG. 40 provides a perspective view 4000 of an embodiment 3600 in which the central portion is configured as a ring 4010 of flexible material, from which the arms extensions 4014 carryings tabs 4014A protrude in substantially opposite directions, FIGS. 39A, 39B illustrate a related embodiment 3900. Here, the flexible foreskin stopper 3900 is shown in two different views to outline the shape of the central portion 3910, which is this implementation includes a columnar tab 3910A and two wall-like protrusions 3910B sandwiching the columnar tab 3910A in-between. The protrusions 3914A can bee seen extended from the arms 3914 on both sides thereof. The flexibility of the embodiment 3900 manifests, at least in part, by the ability to reversibly flex the wall-like protrusions 39100B away from and/or towards the columnar-tab 3910A, as well as the ability to at least stretch and/or bend and/or twist not only the arm extensions 3914 but also the protrusions 3914A.

The flexibility of the embodiment 4000 manifests, at least in part, by the ability to reversibly stretch and/or bend and/or twist the ring-shaped central portion 4010 in substantially any direction, as well as the ability to at least stretch and/or bend and/or twist not only the arm extensions 4014 but also the protrusions 4014A.

Figure 41A:
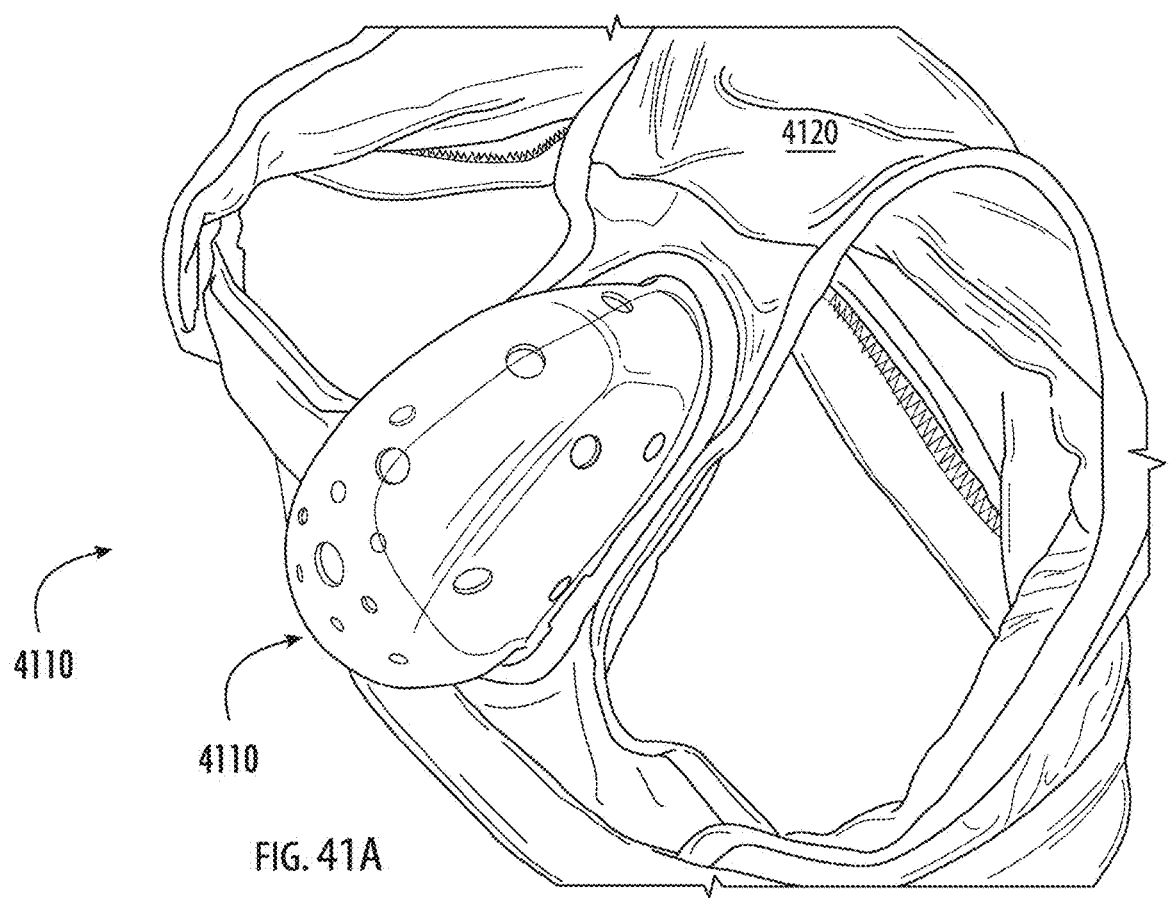
Figure 41B:
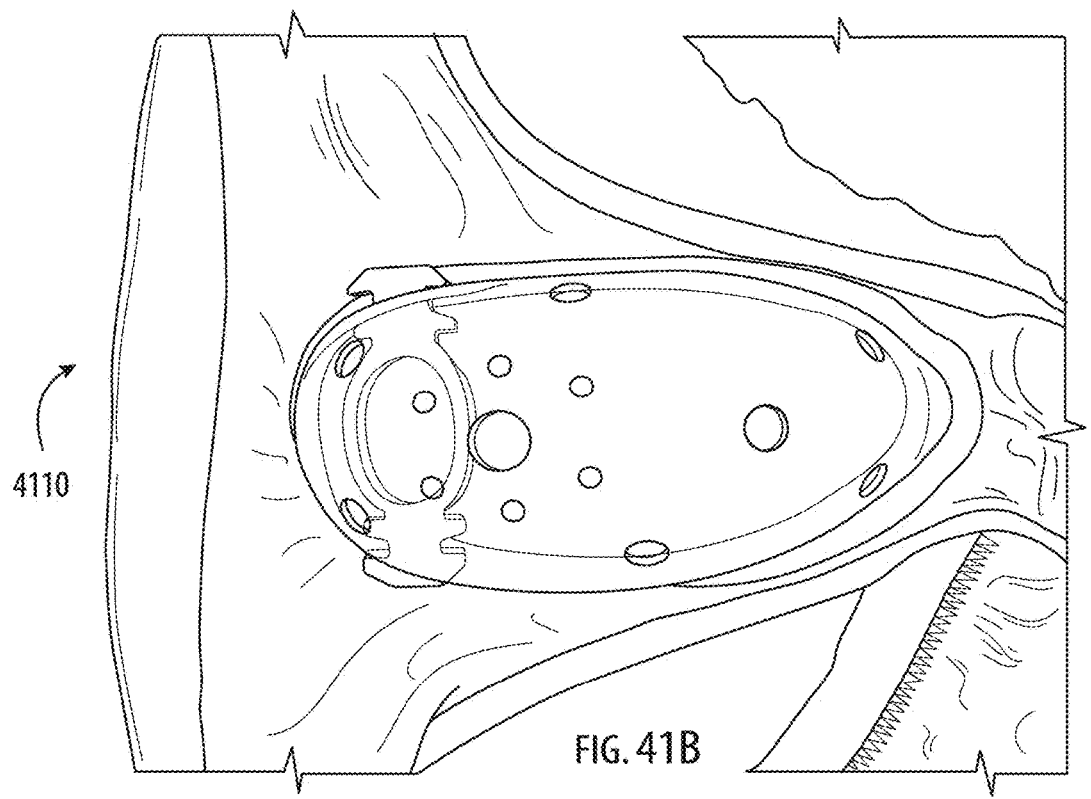

FIG. 41A illustrates a portion of an embodiment 4100 of the device in which an implementation 4110 of the protective cup carries multiple throughout openings of holes in a wall of the cup and is attached to the piece of underwear 4120 of a male user. FIG. 41B shows the portion from FIG. 41A additionally equipped with the embodiment 4000 of the flexible stopper unit, visibly removably affixed to the cup 4110 as a result of pulling the arm extension 4014 of the unit 4000 through the opposing each other openings in the cup 4110.

A skilled artisan will readily appreciate that substantially any of the embodiments illustrated in FIGS. 23, 28, 30, 36 can be operated, in contact with the shaft of the penis, at different distances from the body of the user—for example, be installed in substantial proximity of or in contact with the glans or away from the glans and closer to the body while securing the retracted and inverted foreskin. To vary the distance separating a chosen of these embodiments from the body of the user, a multiplicity of openings in the protective cup 2110 can be formed, and extensions arms such as 2310, 2814, and 3614 can be pulled through and secured in different pairs of such openings at different distances from the body of the user. As a result, any of these embodiment can be operated to perform at least three functions: —to retract foreskin backward to assist topical application of ointments for diseases such as balanitis, lichen sclerosis, etc. to eliminate the need for circumcision; —to pull foreskin forward (when the ring portion of the embodiment is disposed above the non-inverted foreskin, for example) to alleviate phimosis—in this case the silicone ring (stopper) may be attached toward the front of the cup and the ring portion might attach differently to the foreskin, such as via clips; and even—act as a protector after circumcision to allow the wound to heal. Accordingly, the scope of invention also includes foreskin manipulation with the use of an embodiment of the device (such as one of these described above). The presence of the undergarment cup 2110 in at least some of the embodiments of the device may be additionally employed to prevent sexual use while device is being employed.

In particular, implementations of the foreskin manipulator device can be appropriately structured to treat phimosis (a condition known to manifest in the foreskin being too tights to be pulled back over the head of the penis) and paraphimosis (a condition where the foreskin cannot be returned to its original position after being retracted).

The implementation of the device for treatment of phimosis assumes that the outer dimension of the central portion of the flexible stopper unit is smaller than a maximum diameter of a glans of the penis such that, when the flexible central body is brought in contact with a tip of the penis and foreskin covering the tip and when the arm extensions are pulled respectively through first and second openings from inside the protective cup and affixed to the cup in tensioned contact with the cup, the flexible central body applies at least outwardly radial pressure to the foreskin along an axis of a chosen arm extension. In a specific case when the flexible stopper unit is configured according to the embodiment 4000, the diameter of the ring 4010 is chosen to be smaller than a maximum diameter of a glans of the penis such that, when the ring is brought in contact with a tip of the penis and when the first and second arm extensions are pulled respectively through first and second openings from inside the protective cup and affixed to the cup in tensioned contact therewith, the ring applies at least outwardly radial pressure to the foreskin along an axis of a chosen arm extension.

The implementation of the device for treatment of paraphimosis assumes that the ring 4010 is dimensioned such that, when the ring is installed onto and in contact with a shaft of the penis having the glans and mucosal membranes exposed and when the first and second arm extensions are pulled respectively through the first and second openings from inside the protective cup and affixed to the cup in tensioned contact therewith, the ring applies to the foreskin a force directed along the shaft. Generally, the implementations configured in accord with, for example, embodiments of FIGS. 38, 39A, 39B, 40 are such that the foreskin stopper unit includes an elastic material configured to maintain the penis under radial pressure when the ring is in contact with the shaft. Manipulation of the foreskin with the use of a device discussed in reference to FIGS. 38, 39A, 39B, 40 includes at least positioning the foreskin stopper unit inside the protective cup of the underwear worn by the user with the first and second arm extensions being removably affixed to the protective cup; bringing the flexible central body in contact with either the glans and an edge of the foreskin that covers a portion of the glans, or a shaft of the penis having the glans and mucosal membranes exposed; and applying a first pressure to the foreskin directed substantially radially with respect to the shaft by stretching the first and second arm extensions affixed to the protective cup.

In addition, a second pressure can be applied to the foreskin directed substantially along the shaft. Upon maintaining such spatial coordination between the embodiment of the device and the penis, the user may take the following step progressively leading to alleviation of the phimosis (or paraphimosis) condition:

Disengage the foreskin stopper unit from the glans and remove the foreskin stopper unit from the protective cup;

With the use of an auxiliary foreskin stopper unit that includes an auxiliary flexible central body dimensioned to be positioned in contact with the at least a front portion, and auxiliary first and second arm extensions protruding from the auxiliary flexible central body in substantially opposite directions (here, the protective cup is configured to have the auxiliary foreskin stopper unit removably and repositionally affixed to and inside the protective cup via cooperation of the auxiliary first and second arm extensions with the protective cup):

bring the auxiliary flexible central body in contact with either the glans and an edge of the foreskin that covers an auxiliary portion of the glans, or the shaft of the penis having the glans and mucosal membranes exposed;

apply third pressure to the foreskin directed substantially radially with respect to the shaft by stretching the auxiliary first and second arm extensions affixed to the protective cup; and maintaining such third pressure for a predetermined period of time.

A person of ordinary skill in the art will readily appreciate that references throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. Accordingly—as the skilled artisan will readily appreciate—while in this specification the embodiments have been described in a way that enables a clear and concise specification to be written, it is intended that substantially none of the described embodiments can be employed only by itself to the exclusion of other embodiments (to the effect of practically restriction of some embodiments at the expense of other embodiments), and that substantially any of the described embodiments may be variously combined or separated to form different embodiments without parting from the scope of the invention. In particular, it will be appreciated that all features described herein at applicable to all aspects of the invention. For example, a combination of the features of the embodiments of substantially any of FIGS. 2, 4, 6, 10, 13, 15, 17, 19, 21, 23, 28, 30, 32, 35A, 36 with one another can be formed to generate an a related specific embodiment of the device of the invention for practical use, and each of those combinations remain within the scope of the invention as a given embodiment.

In addition, when the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Therefore, while generally the implementation of the invention is directed to a device for maintaining retraction and inversion of a foreskin of a male user (while keeping glans of an uncircumcised penis and mucosal membranes exposed), in which device includes a foreskin stopper unit dimensioned to be positioned onto and in contact with a shaft of the penis with the exposed glans and mucosal membranes against a neck of the glans, and in which device (1) the stopper unit is configured to press against the glans to form an anchoring feature for said stopper unit to create a reaction force for sustained inversion of the foreskin, and/or (2) the stopper unit is connected and affixed to a component of undergarment of the user, a specific embodiment of such device in which the stopper unit contains one or more of the following structural features—a) a tubular component containing at least one of a hollow cylindrical element and a hollow conical element a diameter of at least one of bases of which is dimensioned to anchor against the glans and a length to cover at least a portion of the inverted foreskin with the exposed mucosal membranes when installed over the shaft; b) a ring dimensioned to completely circumscribe the shaft at the neck of glans; c) a curved clip configured as a coil spring; d) multiple arched arms, each dimensioned to contact the shaft along a portion of a circumference thereof at the neck of glans while leaving a portion of said circumference exposed and not directly connected with one another; and e) multiple rods or tubes, each dimensioned to be installed in contact with and across the shaft at the neck of glans—is also a stand-alone related embodiment of the invention. Similarly, while the general scope of the method of maintaining a foreskin of a penis of a user in a retracted and inverted position (with a device that includes a foreskin stopper unit dimensioned to be positioned onto and in contact with a shaft of the penis with exposed glans and exposed mucosal membranes) is that including the actions of inverting the foreskin back to expose the glans and the mucosal membranes and disposing at least a first portion of the foreskin stopper unit at a shaft of the penis and over the inverted foreskin to hold the inverted foreskin in place (as a result of at least one of anchoring the device against at least one of glans of the penis and anchoring said stopper unit at an undergarment of the user), in at least one specific embodiment of the method the action of disposing may include one or more of the following steps: a) positioning a tubular component of the stopper unit over the shaft with an edge of the tubular component against the glans, wherein the tubular component contains at least one of a hollow cylindrical element and a hollow conical element a diameter of at least one of bases of which is dimensioned to anchor against the glans and a length to cover at least a portion of the inverted foreskin with the exposed mucosal membranes when installed over the shaft; b) locating a ring of the stopper unit over the shaft to completely circumscribe the shaft at the neck of glans; c) disposing a curved clip of the stopper unit onto the shaft; d) locating multiple arched arms of the stopper unit onto the shaft, each of the multiple arched arms dimensioned to contact the shaft along a portion of a circumference thereof at the neck of glans while leaving a portion of said circumference exposed and not directly connected with one another; and e) contacting each of multiple rods of the stopper unit with and across the shaft.

In operation, the initial retraction of the foreskin may be done by the operation of the device or the user himself who manually retracts and inverts the foreskin using his hands. The design may contact the circumference of the penis and foreskin to create desired pressure to ensure a fixed position of the device on the foreskin. To ensure foreskin retraction, the device requires a reaction force utilizing the glans of the penis, an undergarment, or a combination of both as an anchor for retraction. The topical cream or other medicine is applied on the affected area (in some cases—through perforations in the device) while the foreskin is kept retracted by this device.

The invention should not be viewed as being limited to the disclosed embodiment(s).

The invention claimed is:

1. A method for manipulation of a foreskin of a male user with the use of a device that comprises:
a protective cup dimensioned to be affixed to an underwear of the male user to accommodate and cover at least a front portion of an uncircumcised penis of the user to prevent contact between the at least a front portion and an object outside the protective cup; and
a first flexible foreskin stopper unit including:
 a flexible central body dimensioned to be positioned in contact with the at least a front portion and having a first outer dimension, and
 first and second arm extensions protruding from said flexible central body in substantially opposite directions,
wherein said protective cup is configured to have the first foreskin stopper unit removably and repositionally affixed to and inside the protective cup via cooperation of said first and second arm extensions with the protective cup,
the method comprising:
positioning the first foreskin stopper unit inside the protective cup of the underwear worn by the user with the first and second arm extensions being removably affixed to the protective cup,
bringing the flexible central body in contact with:
 either (i) the glans and an edge of the foreskin that covers a portion of the glans,
 or (ii) a shaft of the penis having the glans and mucosal membranes exposed,
applying a first pressure to the foreskin directed substantially radially with respect to the shaft by stretching the first and second arm extensions affixed to the protective cup,
the method further comprising:
disengaging the foreskin stopper unit from the glans and removing the foreskin stopper unit from the protective cup; and
using an auxiliary foreskin stopper unit that includes:
 an auxiliary flexible central body dimensioned to be positioned in contact with the at least a front portion, and
 auxiliary first and second arm extensions protruding from said auxiliary flexible central body in substantially opposite directions, and wherein said protective cup is configured to have the auxiliary foreskin stopper unit removably and repositionally affixed to and inside the protective cup via cooperation of said auxiliary first and second arm extensions with the protective cup, to perform the following steps:
(a) bringing the auxiliary flexible central body in contact with:
   either the glans and an edge of the foreskin that covers an auxiliary portion of the glans, or the shaft of the penis having the glans and mucosal membranes exposed;
(b) applying a third pressure to the foreskin directed substantially radially with respect to the shaft by stretching the auxiliary first and second arm extensions affixed to the protective cup,
and
(c) maintaining said third pressure for a predetermined period of time.

2. A method according to claim 1, further comprising applying a second pressure to the foreskin directed substantially along the shaft.

3. A method according to claim 1,
wherein the flexible central body includes a ring;
wherein said protective cup includes multiple openings through a wall thereof, and
wherein:
(i) when a diameter of the ring is smaller than a maximum diameter of the glans, said step of bringing includes bringing the ring in contact with a tip of the penis to apply said first pressure under tension created by said stretching;
or
(ii) when the ring is dimensioned to be installed onto and in contact with the shaft of the penis having the glans and mucosal membranes exposed, said step of bringing includes applying said first pressure to the foreskin and the shaft under said tension.

4. A method according to claim 3, further comprising:
with said ring being in contact with the foreskin, applying to the foreskin a force directed along the shaft.

5. A method according to claim 3, further comprising at least one of:
(a) maintaining said positioning for a predetermined period of time, and
(b) applying ointment to the foreskin and/or the glans.

6. A method according to claim 1,
wherein each of the first and second arm extensions contains multiple tabs extending transversely from the respective arm extension, and the protective cup contains multiple openings throughout a wall thereof, and
wherein said protective cup is configured to substantially prevent an occurrence of a disconnect, in absence of external input, between the first and second arm extensions, when pulled respectively through first and second openings of said multiple openings, by keeping said first and second arm extensions under tension.

7. A method according to claim 1,
wherein the flexible central body of the first foreskin stopper unit stretches along an axis of an arm extension, from the first and second arm extensions, when said first and second arm extensions are removably and repositionally affixed to the protective cup.

* * * * *